United States Patent
Gryczynski et al.

(10) Patent No.: US 8,159,676 B2
(45) Date of Patent: Apr. 17, 2012

(54) RATIOMETRIC SURFACE PLASMON COUPLED EMISSION DETECTOR

(75) Inventors: Zygmunt Gryczynski, Fort Worth, TX (US); Ignacy Gryczynski, Fort Worth, TX (US); Evgenia Matveeva, Fort Worth, TX (US); Julian Borejdo, Dallas, TX (US)

(73) Assignee: University of North Texas, Health Science Center at Fort Worth, Fort Worth, TX (US)

( * ) Notice: Subject to any disclaimer, the term of this patent is extended or adjusted under 35 U.S.C. 154(b) by 470 days.

(21) Appl. No.: 12/356,288

(22) Filed: Jan. 20, 2009

(65) Prior Publication Data

US 2009/0218516 A1 Sep. 3, 2009

Related U.S. Application Data

(60) Provisional application No. 61/022,480, filed on Jan. 21, 2008.

(51) Int. Cl.
*G01N 21/55* (2006.01)
(52) U.S. Cl. ............... 356/445; 250/459.1; 250/318; 250/216; 250/458.1; 356/6; 356/335; 356/338; 356/36
(58) Field of Classification Search ......... 250/459.1, 250/458.1, 317, 318, 216; 356/445, 6, 335–338, 356/36
See application file for complete search history.

(56) References Cited

U.S. PATENT DOCUMENTS

| | | | |
|---|---|---|---|
| 6,194,223 B1 * | 2/2001 | Herrmann et al. ............ | 356/445 |
| 7,298,549 B2 | 11/2007 | Muller | |
| 7,318,907 B2 | 1/2008 | Stark et al. | |
| 7,691,648 B2 * | 4/2010 | Nishiuma et al. .......... | 435/288.7 |
| 2005/0053974 A1 * | 3/2005 | Lakowicz et al. ................ | 435/6 |

OTHER PUBLICATIONS

Borejdo, J., et al., "Application of surface plasmon coupled emission to study of muscle." Biophys J (2006), 91:2626-35.
Borejdo, J., et al., "Fluorescence Correlation Spectroscopy in Surface Plasmon Coupled Emission Microscope." Optics Express (2006), 14:7878-7888.
Calander, N., et al., "Theory and simulation of surface plasmon-coupled directional emission from fluorophores at planar structures." Anal Chem (2004), 76:2168-73.
Frey, B. L., et al., "Control of the specific adsorption of proteins onto gold surfaces with poly(l-ysine) monolayers." Anal. Chem. (1995), 67:4452-4457.
Gryczynski, I., et al., Surface plasmon-coupled emission using gold film. J. Phys. Chem. B (2004), 108:12568-12574.

(Continued)

*Primary Examiner* — Gregory J Toatley
*Assistant Examiner* — Iyabo S Alli
(74) *Attorney, Agent, or Firm* — Edwin S. Flores; Daniel J. Chalker; Chalker Flores, LLP

(57) ABSTRACT

The present invention includes methods for ratiometric detection of analytes by surface plasmon coupled emission detection that includes disposing a target on the metal layer of a surface plasmon resonance detection system; coupling a first analyte to a first fluorescent dye and a second analyte to a second fluorescent dye; contacting the first and second analytes to the target on the surface plasmon resonance detection system; and measuring the intensity of a first and a second surface plasmon resonance enhanced fluorescence emission ring, wherein the first and second rings, respectively, quantitatively represents the amount of first and second analyte within 50 nanometers of the metal surface.

17 Claims, 13 Drawing Sheets

OTHER PUBLICATIONS

Gryczynski, I., et al., "Radiative decay engineering: 4. Experimental studies of surface plasmon-coupled directional emission." Anal Biochem (2004), 324:170-82.

Gryczynski, Z., et al., "Fluorescence-sensing methods." Methods Enzymol (2003), 360, 44-75.

Gryczynski, Z., et al., "Minimization of detection volume by surface-plasmon-coupled emission." Anal Biochem (2006), 356:125-31.

Lakowicz, J. R., et al., Intrinsic fluorescence from DNA can be enhanced by metallic particles. Biochem Biophys Res Commun (2001), 286:875-9.

Lakowicz, J. R., Radiative decay engineering: biophysical and biomedical applications. Anal Biochem (2001), 298:1-24.

Lakowicz, J. R., et al., "Radiative decay engineering: 2. Effects of Silver Island films on fluorescence intensity, lifetimes, and resonance energy transfer." Anal Biochem (2002), 301, (2), 261-77.

Lakowicz, J. R., et al., "Directional surface plasmon-coupled emission: A new method for high sensitivity detection." Biochem Biophys Res Commun (2003), 307:435-9.

Lakowicz, J. R., "Radiative decay engineering: 3. Surface plasmon-coupled directional emission." Anal Biochem (2004), 324:153-69.

Malicka, J., et al., "Effects of metallic silver island films on resonance energy transfer between N,N'-(dipropyl)-tetramethyl-indocarbocyanine (Cy3)- and N,N'-(dipropyl)-tetramethyl-indodicarbocyanine (Cy5)-labeled DNA." Biopolymers (2003), 70:595-603.

Malicka, J., et al., "Increased resonance energy transfer between fluorophores bound to DNA in proximity to metallic silver particles." Anal Biochem (2003), 315:160-9.

Malicka, J., et al., "Use of surface plasmon-coupled emission to measure DNA hybridization." J Biomol Screen (2004), 9:208-15.

Matveeva, E., et al., "Metal-enhanced fluorescence immunoassays using total internal reflection and silver island-coated surfaces." Anal Biochem (2004), 334:303-11.

Muthu, P., et al., "Decreasing photobleaching by silver island films: application to muscle." Anal Biochem (2007), 366:228-36.

Neogi, A., et al., "Coupling of spontaneous emission from GaN-AlN quantum dots into silver surface plasmons." Opt Lett (2005), 30:93-5.

* cited by examiner

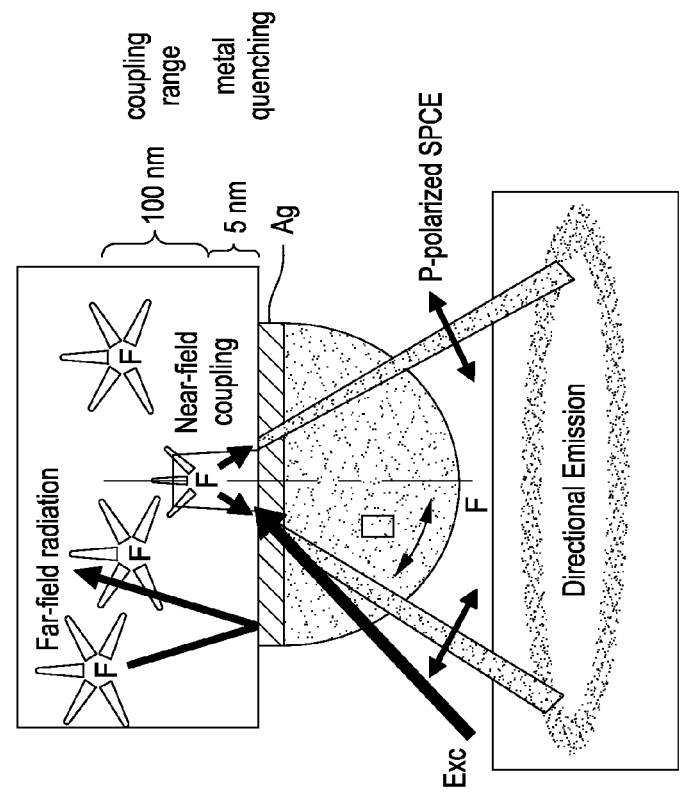
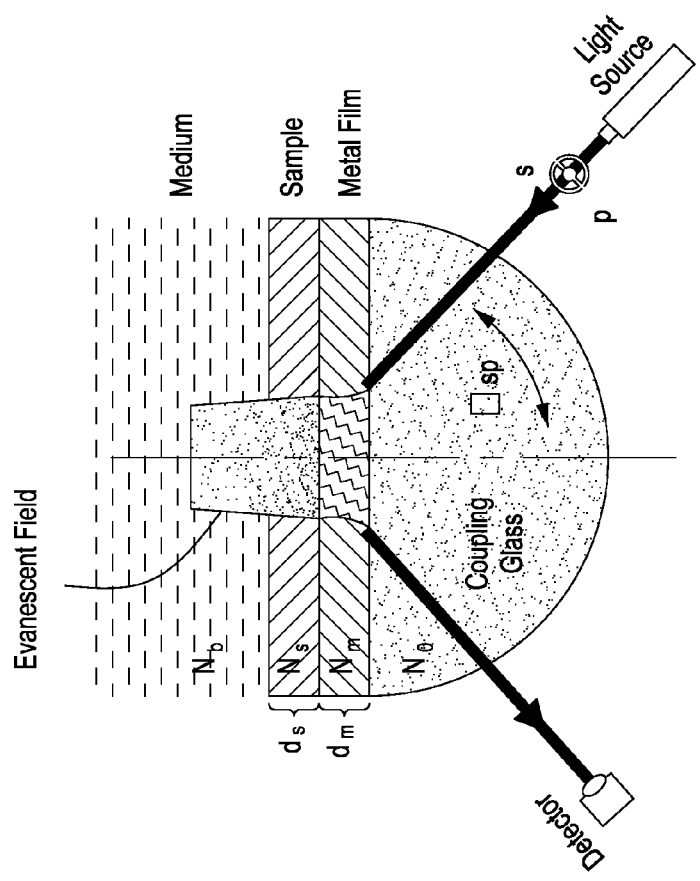
FIG. 3

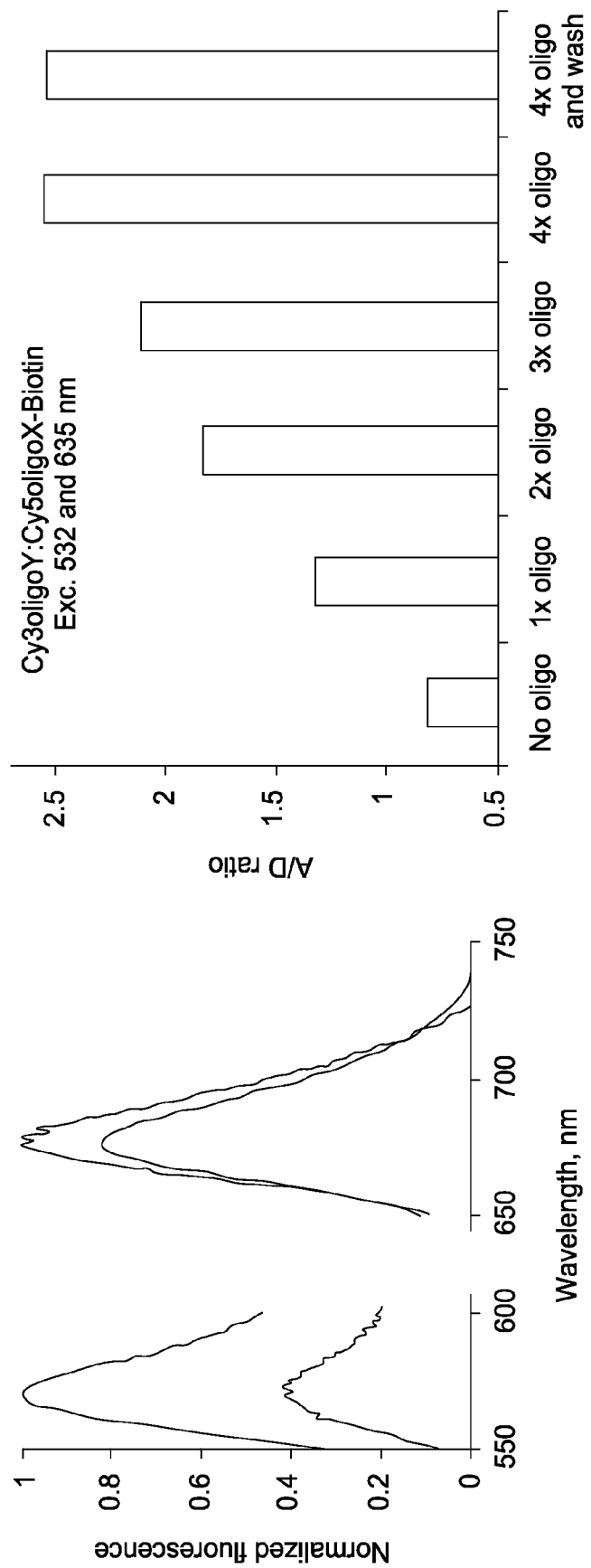

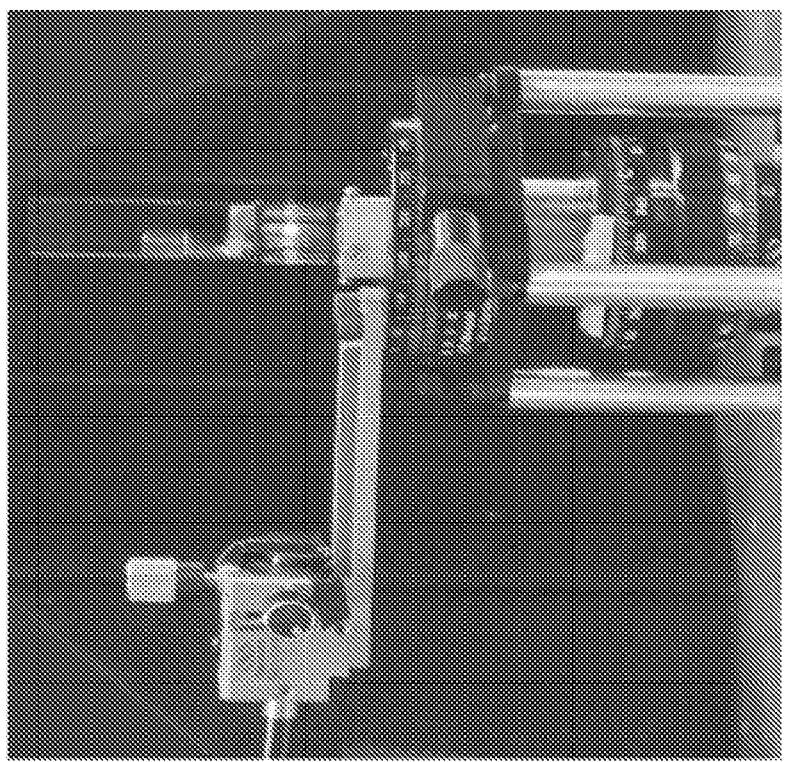
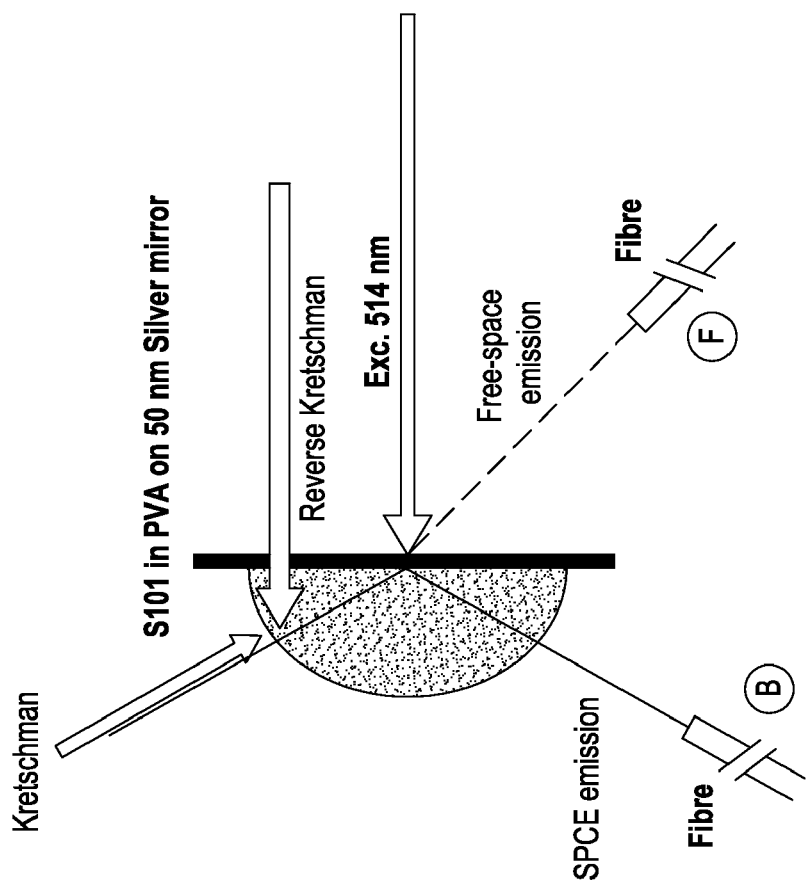
FIG. 10

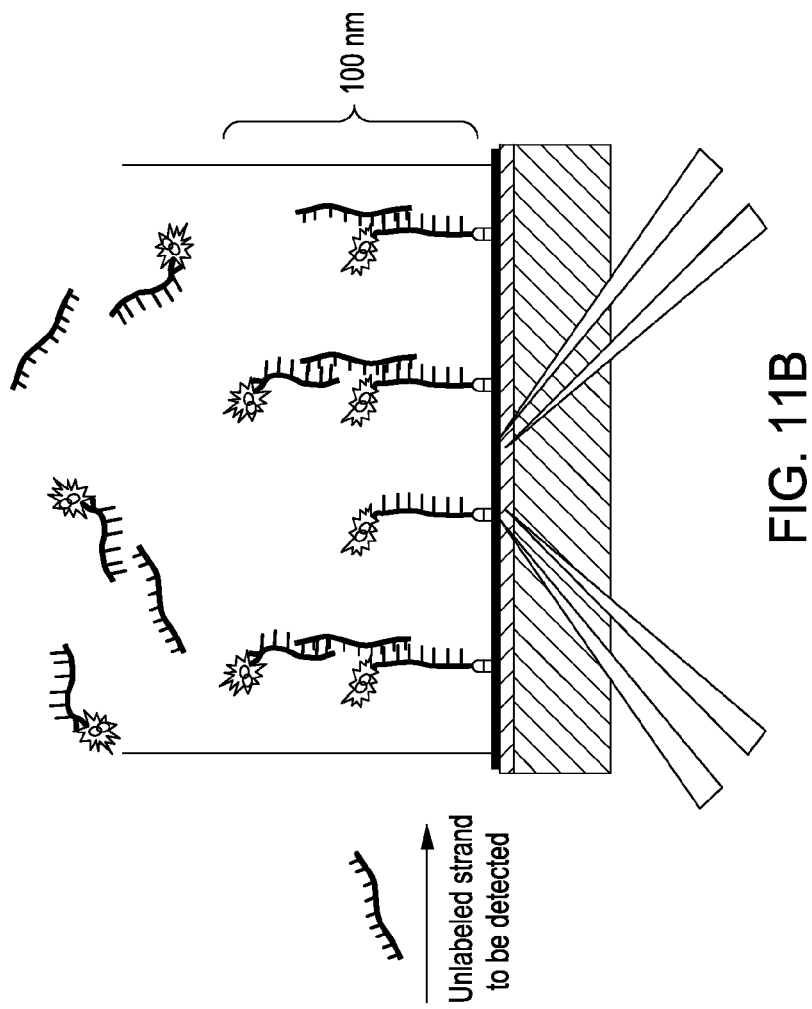
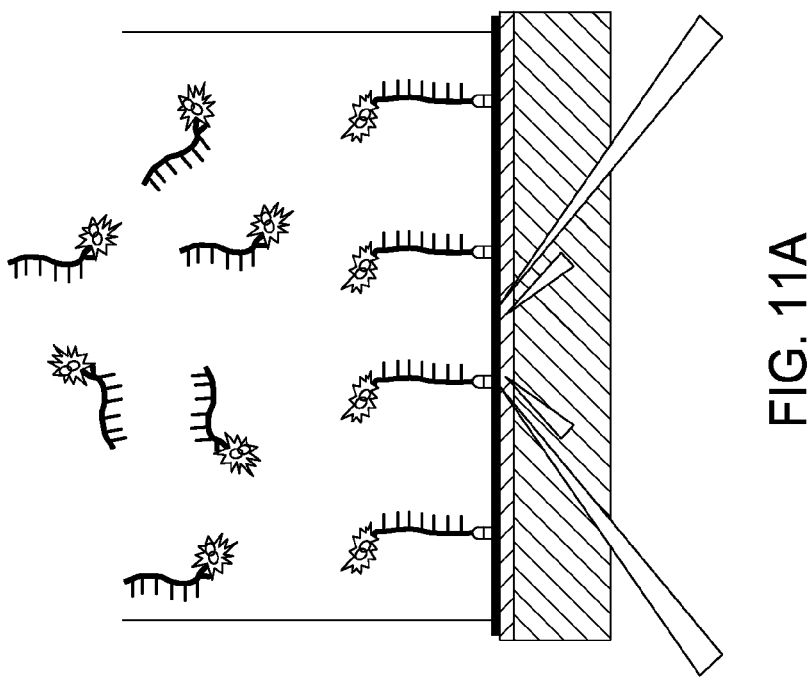

RATIOMETRIC SURFACE PLASMON COUPLED EMISSION DETECTOR

CROSS-REFERENCE TO RELATED APPLICATIONS

This application claims priority to U.S. Provisional Application Ser. No. 61/022,480, filed Jan. 21, 2008, the entire contents of which are incorporated herein by reference.

STATEMENT OF FEDERALLY FUNDED RESEARCH

This invention was made with U.S. Government support under Contract Nos. AR 048622 and CA114460 awarded by the NIH. The government has certain rights in this invention.

TECHNICAL FIELD OF THE INVENTION

The present invention relates in general to the field of fluorescence-based technologies for research in the life sciences, biotechnology, medical diagnostics and other fields.

INCORPORATION-BY-REFERENCE OF MATERIALS FILED ON COMPACT DISC

None.

BACKGROUND OF THE INVENTION

Without limiting the scope of the invention, its background is described in connection with methods for fluorescent detection.

U.S. Pat. No. 7,318,907, issued to Stark, et al., teaches a surface plasmon enhanced illumination system, teaches methods and apparatus for producing small, bright nanometric light sources from apertures that are smaller than the wavelength of the emitted light. Light is directed at a surface layer of metal onto a light barrier structure that includes one or more apertures each of which directs a small spot of light onto a target. The incident light excites surface plasmons (electron density fluctuations) in the top metal surface layer and this energy couples through the apertures to the opposing surface where it is emitted as light from the apertures or from the rims of the apertures. Means are employed to prevent or severely limit the extent to which surface plasmons are induced on the surface at the aperture exit, thereby constraining the resulting emissions to small target areas. The resulting small spot illumination may be used to increase the resolution of microscopes and photolithographic processes, increase the storage capacity and performance of optical data storage systems, and analyze the properties of small objects such as protein and nucleic acid molecules and single cells.

Finally, U.S. Pat. No. 7,298,549, issued to Muller teaches a confocal microscope has a specimen holding device for holding a specimen. The specimen is illuminated by an illuminating unit. An optics unit serves to direct radiation produced by the illuminating unit toward the specimen and to direct the radiation emitted by the specimen toward a detector unit. The confocal microscope also comprises an aperture diaphragm that is placed in the beam path in front of the detector unit. In addition, a focusing lens is provided in the beam path in front of the aperture diaphragm. The focusing lens can be moved in order to adjust the confocal microscope, for example, in order to compensate for thermal stresses.

SUMMARY OF THE INVENTION

The present invention is directed to an apparatus and method for detection of analyzed using Surface Plasmon Coupled Emission (SPCE) detection.

The present invention includes and apparatus and method for ratiometric surface plasmon coupled emission detection by disposing a target on the metal layer of a surface plasmon resonance detection system; coupling at least a first analyte to a first fluorescent dye and at least a second analyte to a second fluorescent dye; contacting the first and second analytes to the target on the surface plasmon resonance detection system; and measuring the intensity of a first and a second surface plasmon resonance enhanced fluorescence emission ring, wherein the first and second rings, respectively, quantitatively represents the amount of first and second analyte within 50 nanometers of the metal surface. In one aspect, the at least first and second fluorescent dyes are selected from 7-Aminoactinomycin D; Acridine orange; Acridine yellow; Alexa Fluor; AnaSpec; Auramine 0; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9, 10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone and Yellow fluorescent protein.

In one aspect of the present invention, the first and second analytes are selected from nucleic acids, polynucleotides, amino acids, peptides, polypeptides, lipids, carbohydrates, vitamins, minerals, cells and tissues and combinations thereof. The surface plasmon resonance detection system may be in a Reverse Kretschmann configuration or a Kretschmann configuration. In another example, the surface plasmon resonance detection system comprises one or more light sources that do not interfere with the emission spectra of the first and second dyes. For example, the present invention may be used to detect surface plasmon enhanced molecules generated from chemiluminescent emissions, bioluminescent emissions, electrochemiluminescent emissions, fluorescent resonance emissions and combinations thereof. In another example, the target is within a cell.

Another embodiment of the present invention is an apparatus and method for ratiometric surface plasmon coupled emission detection by disposing a target on the metal layer of a surface plasmon resonance detection system, the surface plasmon resonance detection system including: a light translucent material; a metal layer disposed on the light translucent material, wherein the thickness of the metal layer is 50 nM or less; a glass prism disposed on the light translucent material opposite the metal layer; a light source capable of exciting two or more surface plasmon enhanced molecules, the excitation source positioned to strike the light translucent material at a first angle; and a light detector that detects emitted light generated by the two or more surface plasmon enhanced molecules at a first and a second angle; the method further including: coupling two or more target specific fluorophores for detection of two or more specific targets in a sample; contacting the two or more target specific fluorophores to the targets in the sample, wherein the sample is on the metal layer; and measuring the intensity of a first and a second surface plasmon resonance p-polarized enhanced fluorescence emission ring for each of the two or more fluorophores, wherein each of the two or more fluorophores generates a separate fluorescence emission ring that quantitatively represents the amount of binding to the two or more targets within 50 nanometers of the metal layer.

In one aspect of the present invention, the two or more fluorescent dyes or fluorophores are selected from 7-Aminoactinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9, 10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone and Yellow fluorescent protein. The two or more analytes may be selected from, e.g., nucleic acids, polynucleotides, amino acids, peptides, polypeptides, lipids, carbohydrates, vitamins, minerals, cells and tissues and combinations thereof. The surface plasmon resonance detection system may be in a Reverse Kretschmann or a Kretschmann configuration. The surface plasmon resonance detection system will also include one or more light sources that do not interfere with the emission spectra of the first and second dyes.

BRIEF DESCRIPTION OF THE DRAWINGS

For a more complete understanding of the features and advantages of the present invention, reference is now made to the detailed description of the invention along with the accompanying figures and in which:

FIG. 3(a) shows one configuration of an SPR device of the present invention (left). At the SPR angle, the reflectivity is strongly attenuated. FIG. 3(b) SPCE model where F is a fluorophore. The excitation energy of fluorophore couples to the surface plasmons and radiates to the glass prism in form of the ring. Far-field radiation is reflected by the metal surface (right).

FIG. 8(a) shows normalized fluorescence spectra of the Cy3-Cy5 hybridized strands on the surface where the Cy5 strand is attached at its 3' end to an avidin coated plate (black lines). Normalized intensities after addition of unlabled oligomer complementary to the anchored Cy5 strand, red lines. FIG. 8(b) The ratio of emission intensities of red (at 679 nm) to green (at 571 nm) increase as the green, Cy3 strand is displaced from the detection volume by unlabeled oligo.

FIG. 10 shows a configuration for measuring angular intensity distribution for SPCE emission. Left—schematic of the configuration. Two excitation modes (Kretschman and Reverse Kretschman) are shown in the figure. Right—photograph of the setup.

FIGS. 11A &11B is a scheme for a DNA sandwich assay.

DETAILED DESCRIPTION OF THE INVENTION

Figure 1B:
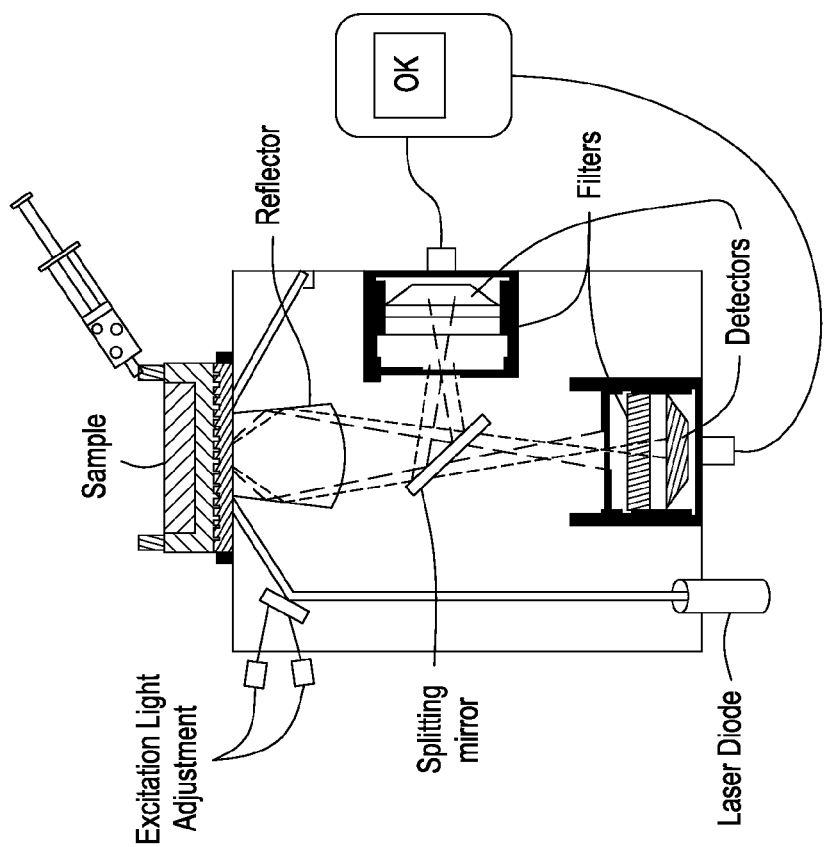
FIG. 1(b) shows a simple ratiometric device for two pin-hole confocal detection of the SPCE fluorescence of two different fluorophores within the SPCE coupling range.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Fluorescence based technologies are important tools for research in the life sciences, biotechnology, medical diagnostics and other fields. Techniques employing fluorescence detection include ELISA, PCR, microarray gene expression chips, other medical diagnostics, forensics tests and increasingly biohazard detection technologies. In many of these techniques, more sensitivity is desired or needed to allow detection of a smaller number of sample molecules and in a smaller volume. The apparatus and method of the present invention is at least 10-100 fold more sensitive than current technologies.

The present invention improves sensitivity to: (a) detect more photons with improved sensitivity and (b) reduce background fluorescence. An ideal technology will employ both, increased photon collection efficiency and provide for more efficient background suppression. Since fluorescence is isotropic (emission in all directions) only ~1-3% of emitted photons are typically detected. While additional mirrors and integrating spheres can increase this percentage, they are expensive and often not workable, particularly for high density arrays. Fluorophores with higher quantum yields can be used, but the improvement is modest. Filters that are used to remove the excitation frequency also decrease sensitivity. While increased concentrations can be used to gain sensitivity for solution measurements, for surface detected experiments, where background is greatly reduced, increased illumination intensity (confocal microscopy) is used. However, more sensitivity is still desired and should be quite marketable.

Sensitivity can be enhanced by SPCE. Clearly, any technique that can increase excitation efficiency, enhance detection efficiency, and reduce background fluorescence (autofluorescence) would overcome current limitations and expand the applicability and sensitivity of the above applications. One such technique, called Surface Plasmon Coupled Emission (SPCE), has recently been developed by the inventors (PI) and others (1-6).

SPCE uses surface plasmons in thin metallic films (gold or silver) (1, 4, 7-10) and has a considerable potential to greatly improve the sensitivity and utility of detection of fluorescence in surface based assays. Theoretical simulations and preliminary data demonstrate that excited fluorophores near a continuous semi-transparent silver film can efficiently couple to surface plasmons and "emit" into the glass substrate behind the metal film at sharply defined, wavelength-depended angles. SPCE displays the following very favorable characteristics for many applications:

1. Directional rather than isotropic emission that allows collection of up to 50% of emitted light.
2. Enhanced surface-localized excitation due to a Surface Plasmon Resonance (SPR) amplified evanescent field where reabsorption is minimized.
3. Background suppression by selective collection of emissions only from regions very close to the surface (50-100 nm).
4. Intrinsic spectral resolution of different fluorophores with minimal optical components.
5. Very small detection volumes down to 2×10-18 liters (11, 12)

SPCE Ratiometric Detection of the present invention. The advantage of SPCE with a ratiometric detection strategy in which the signal is between a fluorophore from the sample of interest and an internal standard fluorophore is disclosed. Such ratiometric methods have a number of advantages (13): (a) measurements are independent of the excitation source and cancel out most variations within or between sources; (b) variances due to sample autofluorescence, ambient light, sample scattering, and reabsorption are often canceled out; and (c) the ratiometric signal does NOT depend on the probe concentration. So, any change in the receptor density on the surface (i.e. dissociation) due to assay requirements will not affect a ratiometric signal. This greatly simplifies the measurement and allows sensing with relatively inexpensive devices.

The present invention is a new generic, ratiometric SPCE technology including the development of a prototype simple sensing device. This will be shown to improve sensitivity (lowest detected concentration) by about 100 fold over solution measurements and by about 10-fold over current state of the art for surface detected experiments (TIRF, Total Internal Reflection Fluorescence). One example of the SPCE device of the present invention is described in detail with reference to sensitive detection of oligonucleotides generally and specifically micro-RNA (mi-RNA).

It was found that wavelength-resolved SPCE is a very sensitive and reliable technology for ratiometric sensing and detection of surface bound oligo-DNA strands in clean buffers and in a 'dirty matrix' such as reconstituted plasma and cell extracts (source of miRNA). About 100-fold and 10-fold improvements over solution and TIRF techniques, respectively, will be shown in terms of lower detectable concentrations.

A simple sensing device was developed that use simple laser diode excitation (i.e. laser pointer) and two photodiode detectors equipped with pinholes. Excitation under the SPR angle excites fluorophores only within the thin sample layer (~100 nm) above a metal surface. Fluorescence couples back to the surface plasmons and is emitted back to the prism under the SPCE angle. Because the SPCE angle strongly depends on the emission color, the green emission (e.g., the Cy3 fluorophore) and red emission (e.g., the Cy5 fluorophore) are intrinsically separated. Importantly, both (green and red) signals initiate on the metal surface layer (~50 nm thick) and the ratio of their intensities (R) is directly related to their relative concentrations on the surface. The DNA strand labeled with the red dye (Cy5) is attached to the surface, and its contribution to SPCE should be constant. The green (Cy3) labeled strand can only be detected by SPCE when is present within ~100 nm of the surface. This means that nearly all green emission is from hybridized strands only. The 'green' strand would be directly related to the miRNA.

Non-limiting examples of fluorophores that may be used with the present invention include: 7-Amino-actinomycin D; Acridine orange; Acridine yellow; Alexa Fluor; AnaSpec; Auramine 0; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9, 10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone; Yellow fluorescent protein, and combinations thereof.

Figure 1A:
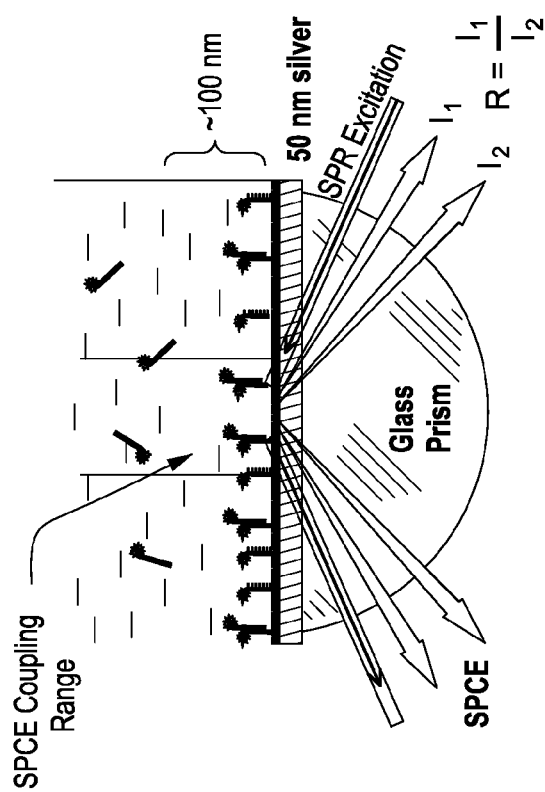
FIG. 1(a) shows that Surface Plasmon Coupled Emission (SPCE) produces two emissions at different angles from a very small region, which can be detected ratiometrically.

FIG. 1(a) shows that SPCE produces two emissions at different angles from a very small region. This can be detected ratiometrically. FIG. 1(b) shows a simple ratiometric device for two pin-hole confocal detection of the SPCE fluorescence of two different fluorophores within the SPCE coupling range. FIG. 1b shows a diagram of a simple but very sensitive device for ratiometric SPCE detection. The directional nature of the SPCE allows it to be focused to a point. This opens a unique possibility to use a simplified confocal format for detection. Two emissions (i.e. green and red) exit the sample under two different angles (zoom in). A simple reflector focuses these two emissions at two different focal points. The SPCE light is split by a dichroic filter/mirror which allows >90% of red light to pass to the bottom detector while reflecting >90% of the green light to the other detector (typical filter used in confocal fluorescence microscopy). In front of each detector will be a moveable pinhole that can be adjusted to transmit only the light emerging from the sample layer under a well defined angle and focused to a point at the pinhole opening. The other color emerging with a different angle (or other stray light) will not pass through the pinhole to reach the detector. Filters may also be used to further reduce background.

In summary, the apparatus and methods of the present invention were used to demonstrate that SPCE can be conveniently used for ratiometric detection of oligos, specifically miRNA. A plate capable of sensing all 78 miRNAs from the fruit fly can use one of the four detection schemes described herein. The SPCE detection device can be optimized and refined in terms of overall size, adaptation to other optical systems, sample size, and limits of detection particularly in dirty matrices. Any application, such as immunological assays, can benefit from the very low detection volume of SPCE.

Solution versus Surface measurements. Measurements of fluorescence at a surface or small volume is and has been a rapidly growing field and includes microarrays, ELISAs, immunoassays, and basic research at the cellular, subcellular, and even molecular levels. Particularly at surfaces, detection and improvement of sensitivity is limited in comparison with bulk solution techniques. Specifically, only a limited number of molecules can be at a surface or within a very small volume in contrast to the much greater number in solution which overwhelms the signals from surface bound ones. To work around this limitation, techniques such as confocal microscopy and Total Internal Reflection Fluorescence (TIRF) are used. Based on our preliminary results and commercial interest (see support letter) SPCE detection will also be one technology that promises the thinnest detection layer for samples well confined to the surface (within $\sim 2 \times 10^{-18}$ liters).

Confocal imaging or detection is where fluorescence is detected only from light that emerges from a well defined space limited by the pinhole size. By focusing fluorescence light into a 20-50 micron pinhole fluorescence microscopy may easily detect volumes down to 10-14 liters. In addition by focusing the laser excitation beam one may limit the lateral resolution to about 200 nm, but the z-axis resolution still remains about 1 micron, and the total volume $\sim 3 \times 10^{-16}$ liters. Thus, confocal microscopy is capable of detecting points throughout a cell or microarray with a depth (z-axis resolution) of about 1 micron and lateral resolution close to one half of the excitation wavelength (routinely ~200 nm).

Figure 2:
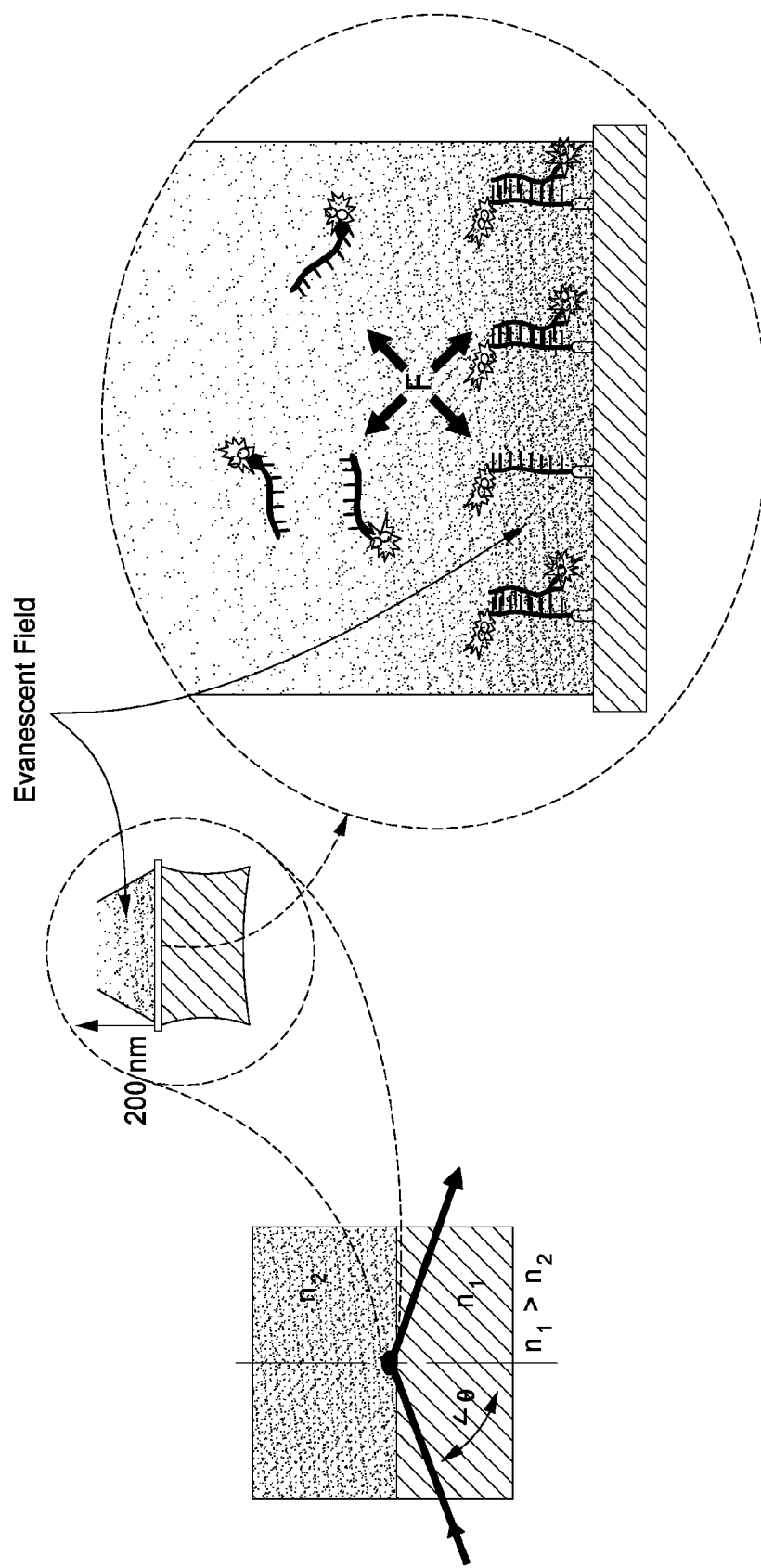
FIG. 2 is a diagram of TIRF excitation and hybridization assay on a surface. While only a small sample layer is excited, fluorescence is partially isotropic.

FIG. 2 shows TIRF excitation and hybridization assay on a surface. While only a small sample layer is excited, fluorescence is partially isotropic.

Total Internal Reflection Fluorescence (TIRF). When light strikes the interface between materials of different refractive indices, light may be partly refracted and partly reflected. However if the incident angle is greater than a certain angle, then impinging light will be totally reflected back into substance with the higher refractive index (FIG. 2 square). However, at the interface where light is totally reflected an 'evanescent wave' is set up across the interface or boundary surface. This evanescent or transitory wave is an electromagnetic field that decays rapidly and exponentially by distance from the interface. It is strongest within a third of the wavelength of the impinging light. This evanescent field can excite fluorophores in the very small region at the boundary where total internal reflection occurs. The emission on the interface is not fully isotropic with a dominant part going into the higher refractive index medium. However it is not as highly directional as SPCE (see below).

SPCE technology combines characteristics of Surface Plasmon Resonance (SPR, an absorption technique) and Total Internal Reflection Fluorescence (TIRF). A brief discussion of plasmons and SPR, is provided as further background for SPCE.

Plasmons are quantized collective oscillations of free electrons (i.e. plasma) usually induced by impinging electromagnetic radiation (photons). Surface plasmons are those confined to a surface, often in a metal film. These surface plasmons can interact very strongly with light especially with surface electromagnetic waves or oscillations propagating along the interface. The resonant frequencies of these oscillations are very sensitive to changes on the boundary conditions induced by the adsorption of molecules to the metal surface that result in change of adjunct dielectric constant. This is surface plasmon resonance (SPR).

The (SPR) phenomenon has been successfully used for biomolecular detection and for studying bioaffinity reactions on surfaces for over 20 years (14-19). A typical SPR experiment uses a 50 nm layer of gold (or silver) on a glass substrate as shown in FIG. 3a. Such a thin metal surface is highly reflective (like a mirror) but displays strong absorption of light impinging under a very well define angle ($\forall$SPR). This effect manifests itself with attenuated reflection and is a result of the resonance excitation of surface plasmons in the metal layer.

FIG. 3(a) shows one configuration of an SPR device (left). At the $\forall$SPR angle, the reflectivity is strongly attenuated. FIG. 3(b) is an SPCE model where F is a fluorophore. The excitation energy of fluorophore couples to the surface plasmons and radiates to the glass prism in form of the ring. Far-field radiation is reflected by the metal surface (right). In the SPR study (FIG. 3(a)), a thin metal film is illuminated through the glass prism at the angle $\forall$SPR. The electromagnetic light wave induces a periodic oscillating evanescent electric field that forces collective planar oscillation of free charges on the metal film (surface plasmons). For a very precisely defined angle, when the component of the impinging light wavevector, k, matches the wavevector of the surface plasmons ksp, surface plasmons oscillation is in resonance with the frequency of incident light. Under such conditions the electromagnetic field efficiently couples to the surface plasmons oscillation, resulting in highly attenuated light reflection. This phenomenon (SPR) is extremely sensitive to small changes of the dielectric constant above the metal film and has been used to measure biomolecule binding to surfaces, as in the Biacore apparatus (http://www.biacore.com).

SPCE: A Surface Plasmon Fluorescence Phenomena in Thin Metal Films. The effects of metallic surfaces on fluorescence have been described in the optical physics literature (21-26). This topic is very complex and the underlying principles are obscure even to many individuals with long experience in fluorescence spectroscopy and fluorescent assay technologies.

Figure 4:
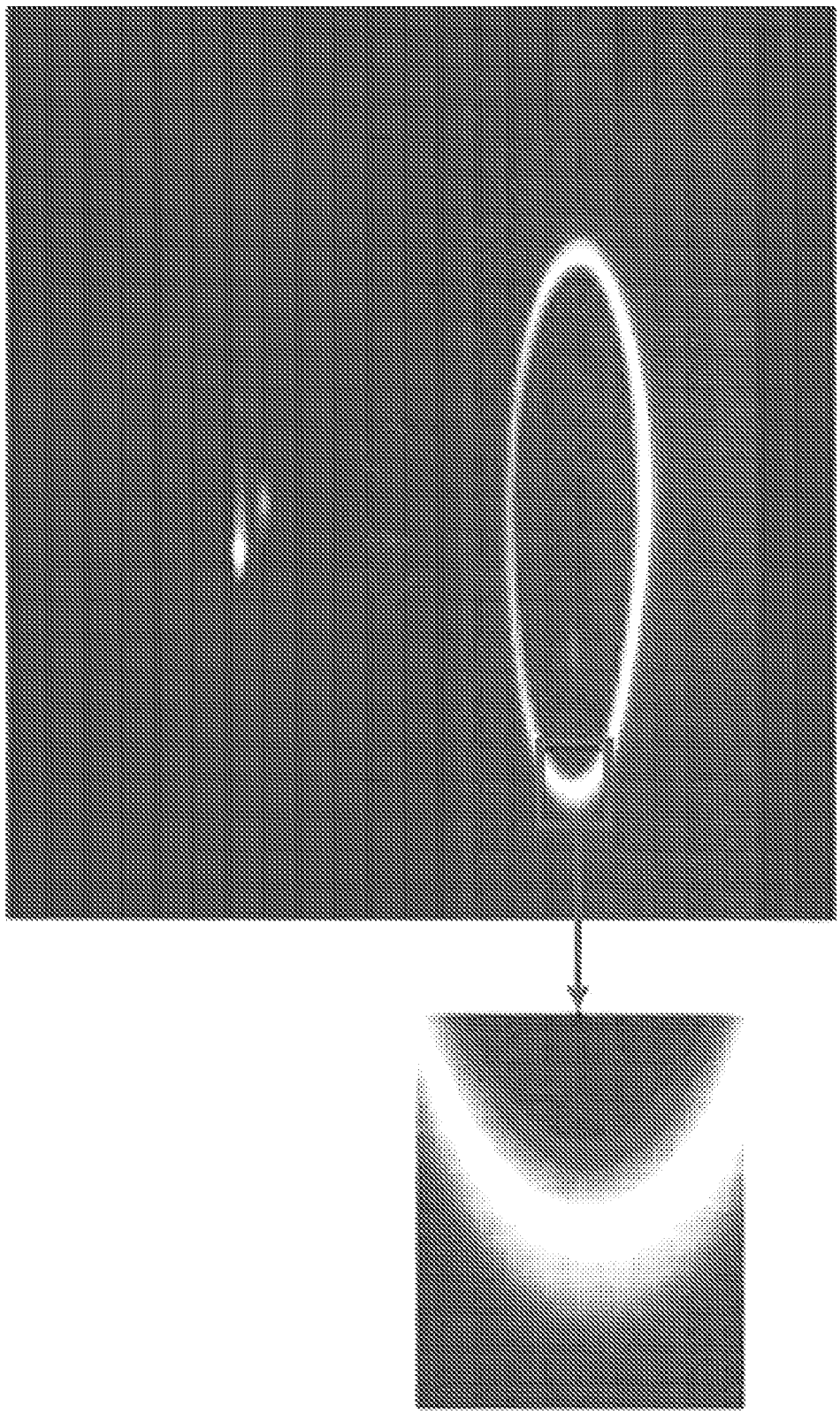
FIG. 4 is a photograph of three surface coated fluorophores emitting by SPCE.

As for SPR, excited surface plasmons in the metal film create a highly enhanced evanescent field penetrating the dielectric above the metal surface up to ~100 nm into the sample to excite the fluorophore, (FIG. 3(b)). Upon excitation a reverse process occurs where the excited fluorophore induces an electromagnetic field that can strongly interact with the free charges in the metal film, inducing the surface plasmons. The frequencies of the induced surface plasmons correspond to those of the fluorophore emission spectrum. This near-field interaction of fluorophore with semi-transparent planar metal surface results in a highly efficient emission coupling through a thin metal film that passes into the glass prism. A very strongly directional emission is observed, which is called the Surface Plasmon Coupled Emission (SPCE). This is shown in FIGS. 3b and 4. The resulting SPCE preserves all the spectral properties of the fluorophore and is highly polarized with a sharply defined emission direction. The coupling highly depends on the distance from the surface and is maximal at 30-50 nm but extends out to 200 nm from the surface. Most of any stray light is reflected by the metal surface.

Thus, SPCE allows for a light collection efficiency of up to 50% (versus ~1-3% for isotropic emission) and intrinsically resolves light of different wavelengths. This is all accomplished with very simple optics (FIG. 1(b)). Such desirable properties can result in a wide range of simple, inexpensive, and robust devices with generic usefulness in biology, medicine, forensics, and other fields. It is important to note that the directional SPCE is not due to reflections, but due to the coupling of the oscillating dipoles of the excited fluorophores with surface plasmons on the metallic surfaces, which in turn radiate into the glass substrate from where they can be focused and detected.

FIG. 4 shows a photograph of three surface coated fluorophores emitting by SPCE (8). The optical configuration can also collect a large fraction (nearly 50%) of the intrinsically resolved emissions (FIG. 1(b)). The intense emissions and wavelength resolution of SPCE are shown in FIG. 4. For this experiment a mixture of rhodamine 123 (R123), sulforhodamine 101 (S101) and pyridine 2 (Py2) in PVA was spin coated to a sample thickness of ~30 nm onto a 50 nm thick silver film on a quartz plate. For these dyes, emission spreads from green to red. Since the refractive index of light strongly depends on wavelength, the angles of emission under SPCE conditions will be intrinsically different for each wavelength or color of light. This effect is so dramatic that the different colors can be seen by eye as shown in FIG. 4. (Photograph taken on a white screen). The resolution is strikingly captured by an inexpensive detector in a digital camera.

Thus, SPCE technology offers several advantages over TIRF technology:
1. The thickness of the coupling layer in the SPCE experiments can be in the range of 50 nm to 100 nm as compared to over 300 nm for TIRF. This results in a smaller well defined detection volume below $2 \times 10^{-18}$ liters. This is 3-fold smaller than for TIRF (11, 12). In effect the power flow for TIRF and SPCE in similar experiments can be comparable. However, the SPCE signal originates from much a smaller sample volume with smaller number of sample molecules.
2. SPCE experiments give superior background suppression. The metallic surface reflects (>90%) of light in the bulk solution due to the high metallic surface reflectivity (over 90% of the light originated in the bulk solution is reflected by the metallic surface and never gets to the prism or detector). For comparison, dielectric interface (water/prism) of TIRF reflects only 5% to 10% of such unwanted light.
3. A very significant SPCE advantage is that the emissions are much more directional in TIRF, allowing more efficient light collection.
4. The excitation evanescent wave in SPCE experiments with SPR excitation (Kretschmann) excitation is much stronger than in TIRF, allowing attenuation of the excitation intensity that results in lower optics/sample background.

In summary, the coupling efficiency for TIRF and SPCE are comparable, but the background contribution in TIRF is incomparably higher and it has less directional emission. Thus, the signal-to-noise ratio is much better for SPCE allowing 10-20 fold better sensing sensitivity. Also, our SPCE microscopy data on muscle fibers indicated there is better dye photo-stability in SPCE experiments (27, 28).

Figure 5:
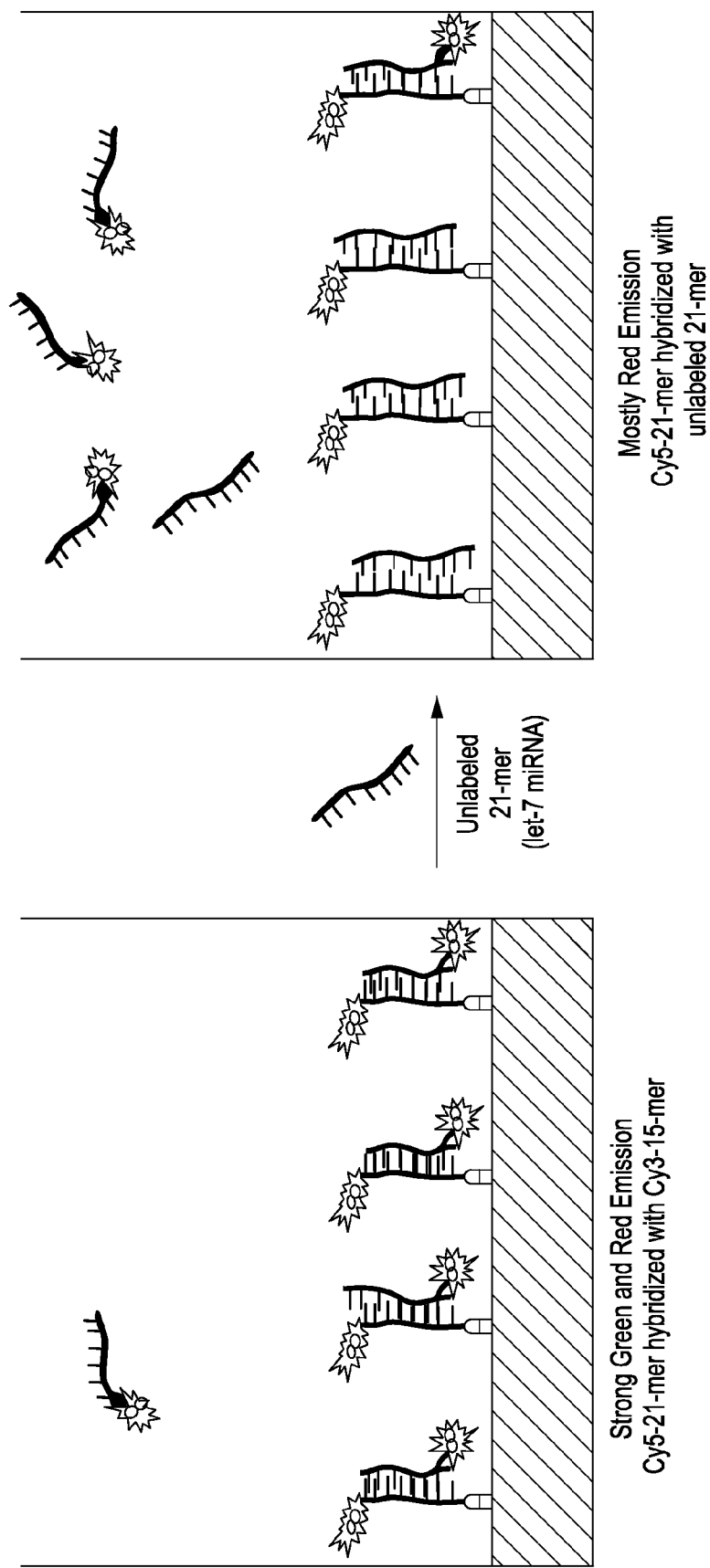
FIG. 5 shows a scheme for ratiometric sensing of oligos by surface fluorescence measurements.

Micro-RNAs (miRNAs). For development and improvement studies, a class of oligonucleotide was sought that not only would lead to a product itself, but also show the potential of ratiometric SPCE detection for other oligos and other biomolecules of interest. Any chosen sequences should be long enough to hybridize readily and be stable but be labile at ~50° C. to allow for rehybridization with a full length complimentary strand or a shorter complimentary strand (12-15 nt). As shown in FIG. 5, this shorter, fluorescently labeled strand would be displaced by the full length strand to be detected (labeled or unlabeled). It should also be long enough to be unique yet not so long to make its chemical synthesis long or too expensive.

The class of RNAs called micro-RNA fit these constraints. They are 21-23 nucleotides (nt) long, and their sequence is well known for many eukaryotic species. Also, there are a limited number of them so large arrays would not be needed. For fruit fly, there are ~78, for humans ~475 (29). These sequences are of keen interest to researchers studying translation or gene expression. They are found in most eukaryotic organisms and a few, like let-7 are conserved across many species. They do not code for proteins but rather function to down regulate mRNA transcription by binding with partial complementarity to many different mRNAs. In contrast to oligonucleotide sequences specific to biohazard agents that are of interest, their sequence is known. Thus, an easy method of detecting specific ones with inexpensive equipment would be a marketable product. This would entail a slide of 78 areas incontrast to Agilent's that has eight 15K microarrays.

With many advantages of TIRF, SPCE detection should be and is more sensitive, detects a thinner, smaller volume at a surface. Emitted light is intrinsically wavelength resolved. This fact coupled with its very intense direction emission will allow sensitive detection of surface fluorophores with minimal optics, inexpensive.

The studies below are summarized in FIG. 5 and were performed in solution and by TIRF analyses with DNA oligos only (RNA is much less stable and degradable for preliminary studies). While it was designed specifically to detect the 'let-7' miRNA, the scheme is generally applicable to the detection of DNA and RNA be they longer and shorter than 21 nt.

FIG. 5 shows a scheme for ratiometric sensing of oligos by surface fluorescence measurements. In the basic setup, a 21-mer DNA strand, complimentary to let-7, is labeled with a 5'-Cy5 dye and 3' biotin. This dual labeled strand is then hybridized to a complementary 15-mer labeled with ~5'-Cy3 dye. A strand of 15 nt was chosen so as to be stable at ambient temperature but displaceable at 50° C. by a full length complimentary strand. Also these lengths were chosen to allow detection of hybridization by FRET in solution. The let-7 complementary 21-mer with the 5'-Cy5 and 3'-bioteg (biotin triethylene glycol) can be anchored to an avidin coated surface (single or double stranded). All the DNA strands used are shown in Table 1 and were highly purified by RP-HPLC.

These Cy3 and Cy5 labeled oligos (A and C of Table 1) were allowed to hybridize first in solution. Subsequently their fluorescence was studied in solution and by TIRF after anchoring to an avidin coated plate. Their emissions at ~670 nm (Cy5) and ~570 nm (Cy3) were determined. Next, the unlabeled 21-mer (i.e., let-7 analog) was added and the systems heated to 50° C. for 10 min to facilitate exchange and rehybridization. Data below show that the longer unlabeled 21-mer displaces the labeled Cy3-15-mer as illustrated in FIG. 5. For TIRF surface experiments, this would allow most of the green Cy3 labeled 15-mer to move outside the TIRF coupling distance (FIG. 5). Thus, the ratio of red to green emission would greatly increase. In solution any change in the ratio would be due to hybridization and change in FRET.

TABLE 1

Labeled and non-labeled oligonucleotides used for the
ratiometric detection of let-7 miRNA.

| Oligo Sequence | Labels/length | Abbreviation |
|---|---|---|
| A 5'-(Cy5)ACTATACAACCTACTACCTCA(Bioteg)-3' | Cy5-21 mer-Biotin | Cy5-oligoX-Biotin |
| B 5'-ACTATACAACCTACTACCTCA(Bioteg)-3' | 21 mer-Biotin | oligoX-Biotin |
| C 5'-(Cy3)TGAGGTAGTAGGTGG-3' | Cy3-15 mer- | Cy3-oligoY |
| D 5'-TGAGGTAGTAGGTTGTATAGT-3' | 21 mer- | oligoY |

DNA Hybridization in Solution. The Cy3 and Cy5 dyes were selected based on their expected separation distance. When hybridized the two 5' dyes should be separated by 60 Å. The characteristic Forster distance for this dye pair is about 55 Å (26). Therefore, a small FRET (about 10%-20%) is expected and would confirm hybridization. This also allows the hybridization, replacement, and rehybridization to be independently monitored when testing principles of the approach. This has been important for preliminary studies and proof of concept experiments. For all studies, solutions of oligos were made in 50 mM Tris, pH 7.3. Hybridization was effected by heating at 50° C. for 10 min.

Figure 6B:
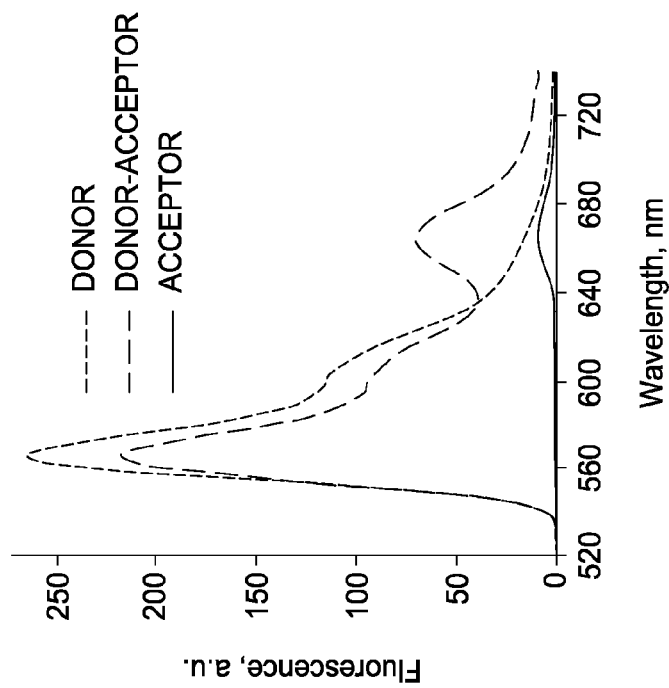
FIG. 6(b) Fluorescence spectra of the hybridized donor control (Cy3oligoY:oligoX-Biotin, C-B)), donor-acceptor (Cy3oligoY:Cy5oligoX-Biotin, C-A), and hybridized acceptor control (Cy5oligoX-Biotin:oligoY, A-D) in the solution (50 mM Tris-HCl buffer, pH 7.3).
Figure 6A:
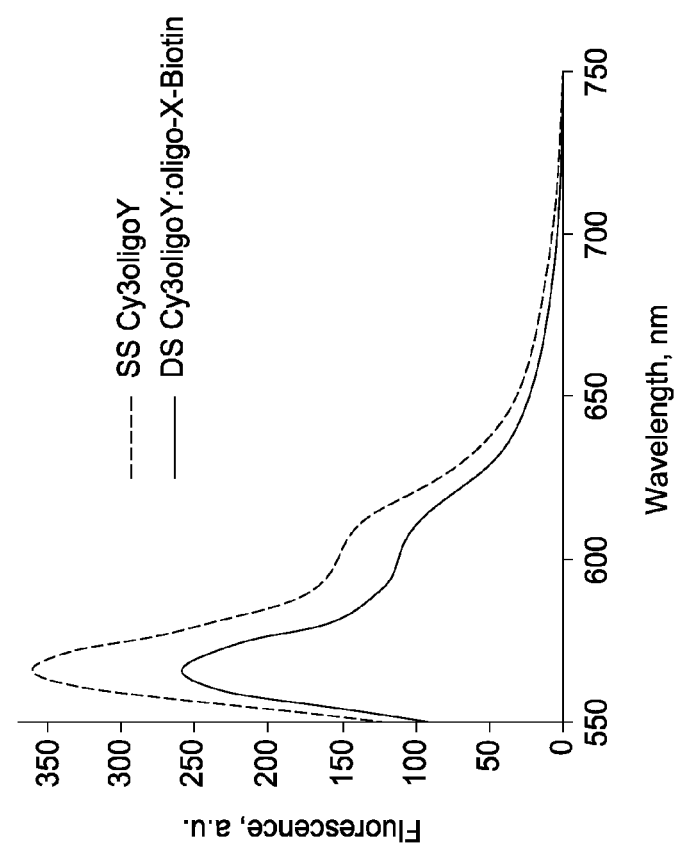
FIG. 6(a) in solution the fluorescence of the Cy3-labled oligo (strand C, Table 1) changes upon hybridization with oligo B.

Fluorescence of the Cy3 labeled strand changed upon hybridization in solution. The B oligonucleotide (21-mer, oligoX-Biotin) without a dye label served to test the change in fluorescence of the FRET donor (Cy3) strand C induced by hybridization into the complementary 21-mer (D). This tests the effect of surrounding nucleotides on the spectral change of the fluorophore to properly estimate Forster distance of 50% transfer (RO) and FRET. FIG. 5a shows that the intensity but not the spectrum changes upon hybridization. This change may be due to intercolation of the dye into the DS oligomer. FIG. 6a shows the fluorescence of Cy3 did decrease upon hybridization with the complementary unlabeled strand (B).

FIG. 6. (a) In solution the fluorescence of the Cy3-labled oligo (strand C, Table 1) changes upon hybridization with oligo B. (b) Fluorescence spectra of the hybridized donor control (Cy3oligoY:oligoX-Biotin, C-B)), donor-acceptor (Cy3oligoY:Cy5oligoX-Biotin, C-A), and hybridized acceptor control (Cy5oligoX-Biotin:oligoY, A-D) in the solution (50 mM Tris-HCl buffer, pH 7.3).

Fluorescence of labeled strands before and after hybridization. FIG. 6b shows the fluorescence spectra of variously hybridized oligonucleotides. These include: (a) 'Donor' with Cy3 labeled strand C, hybridized with unlabeled oligo B); (b) 'Acceptor' with Cy5 strand A hybridized with unlabled strand D); and 'Donor-Acceptor' where strands A and C are hybridized. Excitation at 532 nm was used. The fluorescence of Cy5 acceptor strand is very small due to very low extinction coefficient at 533 nm. In the hybridized system the Cy5 acceptor signal is significantly increased (~670 nm) and donor signal decreases (~570 nm). To confirm that this is due to radiationless energy transfer the fluorescence lifetime of the donor and acceptor was measured. Fluorescence lifetime of the donor should be significantly affected by the presence of acceptor.

Lifetime measurements show the change in fluorescence is due to FRET. Table 2 shows the measured average fluorescence lifetimes for donor (Cy3) and acceptor (Cy5) strands before and after hybridization. As expected the fluorescence intensity and fluorescence lifetime of the dye (donor and acceptor) slightly depend on the presence of complementary unlabeled oligo. This is especially important for the donor, since more properly the lifetime measured in the presence of unlabeled (hybridized) identical strand should be used for the FRET calculation. Hybridization with oligo labeled with Cy5 acceptor additionally changes the fluorescence of the donor. The fluorescence lifetime of the Cy3 donor decreases upon hybridization with Cy5 acceptor indicating a significant ~20% energy (transfer ((0.94-0.75)/0.75). This corresponds well with calculations based on the oligonucleotide's length and our overlap integrals (9). At the same time, the fluorescence lifetime of acceptor practically does not change upon binding its unlabeled complementary strand (1.22 v 1.17 nsec). Replacing the acceptor strand with unlabeled 21-mer returns donor fluorescence lifetimes to expected values (0.75 nsec to 1.36 nsec, acceptor is not present). Thus, the difference above shows the increase in receptor (Cy5) is due to a radiationless energy transfer from the Cy3 donor.

TABLE 2

Average fluorescence lifetime of Cy3-DNA-Cy5
donor-acceptor show expected changes upon hybridization
as obtained by exponential fit.

| Hybridization status | Conditions/Compound | Avg Lifetime (nsec) | $\chi R^2$ |
|---|---|---|---|
| SS | Cy3oligoX | 1.41 | 0.87 |
| DS | Cy3oligoY:oligoX-Biotin** | 0.94 | 0.83 |
| DS | Cy3oligoY:Cy5oligoX-Biotin*** | 0.75 | 0.80 |
| DS | Cy3oligoY:Cy5oligoX-Biotin + competing oligoY | 1.36 | 0.86 |
| SS | Cy5oligoX-Biotin | 1.22 | 0.80 |
| DS | Cy5oligoX-Biotin:oligoY**** | 1.17 | 0.80 |

(Excitation at 475 nm, observation at 605 nm and 665 nm for the donor and acceptor, respectively. $\chi R2$ indicates the goodness of the fit).
*SS, single-stranded; DS, double-stranded.
**Cy3oligoY hybridized with oligoX-Biotin.
***Cy3oligoY hybridized with Cy5oligoX-Biotin (donor-acceptor system).
****Cy5oligoX-Biotin hybridized To see the effect of the fluorescence of the Cy3 oligomer when it is displaced from the Cy5 labeled 21-mer by unlabeled 21-mer (B strand) a series of B strand additions were made. The spectra are shown in FIG. 6a. Excitation was at 510 nm. After each addition of the free, unlabeled oligo the solution was heated up to 52° C. for 10 min, then cooled to 22° C. The down arrow shows the spectrum for the acceptor Cy5-oligoX-Biotin strand hybridized with donor Cy3-oligoY. The other spectra are after addition of 25 nM, 50 nM, and 100 nM of the non-labeled oligo 21oligoY (D), respectively. The increase in fluorescence of the Cy3 donor is due to the loss of its Cy5 acceptor that is being displaced by the unlabeled oligo. The Cy5 dye was not excited by the 510 nm source.

Figure 7A:
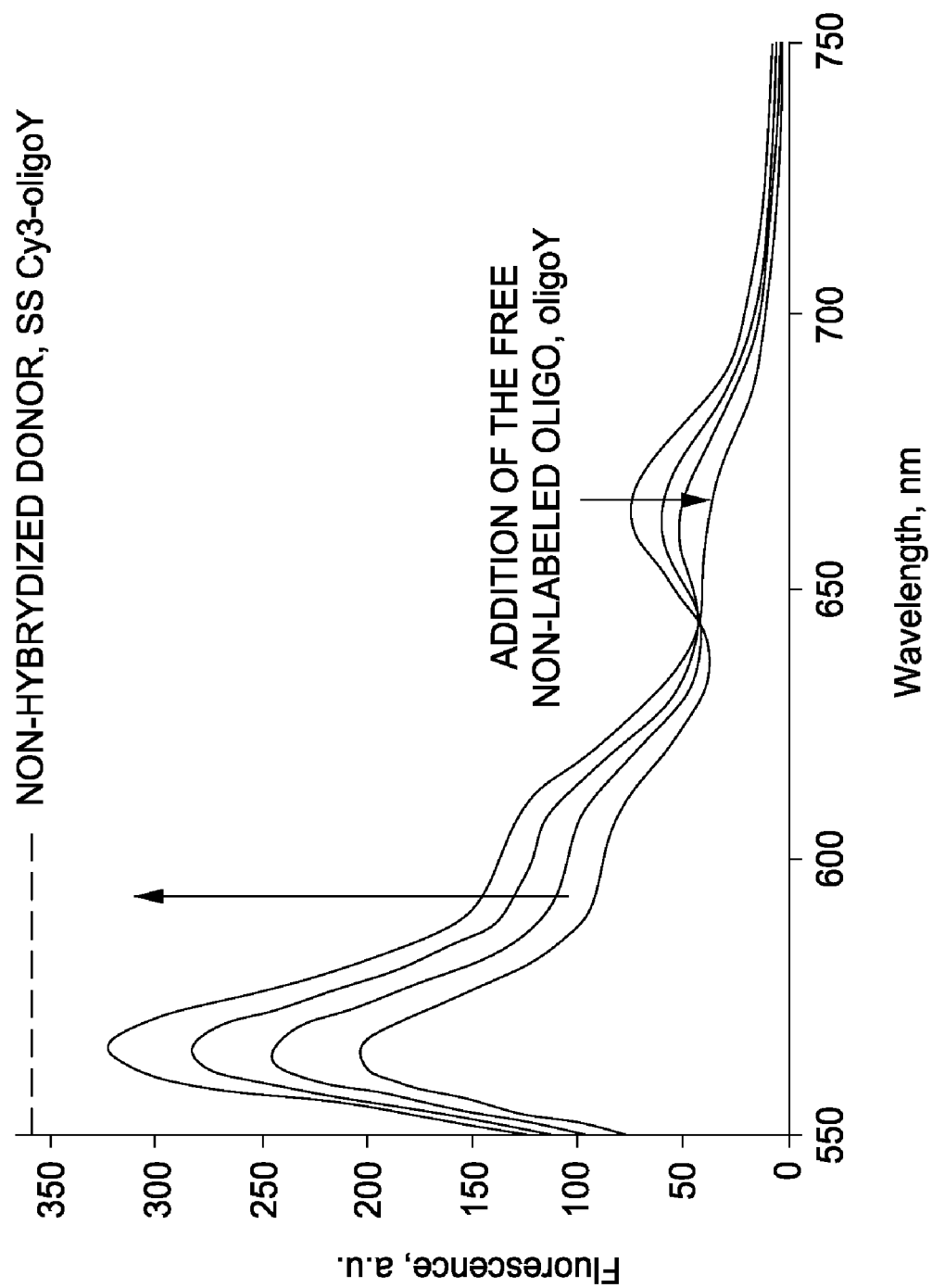
FIG. 7(a) fluorescence of hybridized Cy3 strand (with Cy5 strand) increases as Cy5 strand is displaced with incremental addition of unlabeled complementary strand (B).

FIG. 7(a) shows the fluorescence of hybridized Cy3 strand (with Cy5 strand) increases as Cy5 strand is displaced with incremental addition of unlabeled complementary strand (B). FIG. 7 (*b*) is a diagram of TIRF device used.

DNA hybridization on the surface. In-solution studies confirmed that the fluorescence studies of a set of oligonucleotides labeled with dyes and biotins. The extent of the observed FRET confirmed hybridization and explained how the fluorescence would change in the presence of an acceptor. With confidence that the set of oligonucleotides constitute a very good working system, surface experiments were performed. Total internal reflection fluorescence (TIRF) was used for which the PI and colleagues have considerable experience (30-32).

Figure 7B:
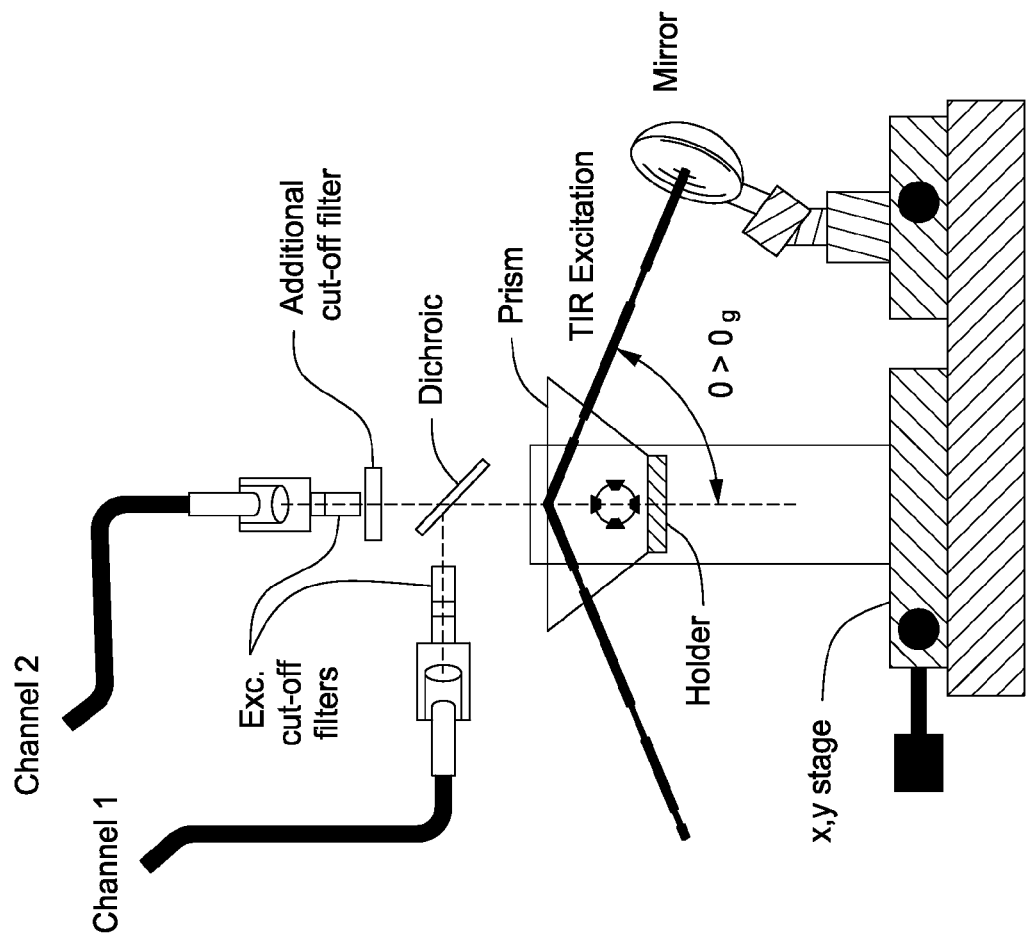
FIG. 7(b) diagram of TIRF device used.

FIG. 7*b* shows the diagram for the TIRF device used for the preliminary results show below. (The phenomenon of TIRF is described for FIG. 2 where the evanescent field penetrates to about 200-300 nm, about half the excitation wavelength). The system has two detection lines to separately detect the Cy3 and Cy5 signals. The 532 nm excitation available from a simple small laser system very strongly excites Cy3 but only minimally excites Cy5 (the absorption of Cy5 at 532 nm is minimal).

A reference signal (red) that is too small can be a problem for testing the ratiometric detection. Unfortunately, there are no simple laser diodes based excitation sources available in this spectral range that will excite both fluorophores. However, as discussed herein this problem can be solved by selecting the pair with efficient FRET. This problem was solved using simultaneous excitation of 532 nm and 633 nm from two separate laser diodes. Combining two excitations allows adjusting the signal readout to be comparable for both, Cy3 and Cy5 dyes. The 633 nm excitation is outside the excitation spectrum of Cy3 and does not disturb its emission.

FIG. 8*a* shows the emission spectra measured for C3/Cy5 hybridized oligomers using TIRF excitation and detection. First, the two strands were hybridized and then immobilized on the surface. After washing with buffer, the fluorescence spectrum was obtained as shown by the black lines in FIG. 7*a* (excitation at 633 nm). Next, the unlabeled 21-mer, complementary to the anchored Cy5 strand was added. After heating to 50° C. for 10 min (no washing), the fluorescence spectrum was obtained and is shown by the red lines in FIG. 7*a*. The decrease at ~570 nm indicates that much of the Cy3 labeled strand was lost from the surface as expected (FIG. 5). On the other hand, a much smaller change was observed for the anchored Cy5 emission at ~670 nm. This indicated that it largely remained attached to the surface throughout the experiment.

FIG. 8*b* shows the change in relative ratio dependence of the red (at ~670 nm) to green (at ~570 nm) emission intensities from the (Cy3oligoY:Cy5oligoX-Biotin) donor-acceptor immobilized on the glass slide in the absence or presence of the free unlabeled oligo (D). This unlabeled oligo complementary to the avidin-biotin anchored one (A). After each addition of the free oligo the hybridization chamber was heated to 52° C. for 10 min, and then cooled to the room temperature. No washing is necessary since the free Cy3 would move out of the TIRF detection range (200-300 nm). The change in the ratiometric signal is over 4 fold. Given the precision of fluorescence measurements, this is a significant and large change. Not shown is the decrease in intensity after each heating step indicative of a loss of avidin anchored oligo from the surface (only surface oligos are detected in TIRF or SPCE) However, as FIG. 7*b* shows, the ratio is intensity independent and capable of giving a reliable measurement even as the density of surface sensors decreases.

Fluorophore Detection Limits. A key sub-aim of this proposal is to show that SPCE measurements will be more sensitive than TIRF ones particularly in a dirty matrix like plasma or blood. To understand the challenge of this goal, the following study was performed with TIRF, currently the state of the art in sensitive surface detection technology by fluorescence detection.

At present there are extensive reports related to single molecule detection (33, 34), so it may be expected that such measurements are easy and straightforward. However, all single molecule fluorescence experiments are performed with microscope optics and high laser excitation energies in restricted volumes to minimize the background relative to the signal. The fluorophores are significantly concentrated, and single molecules are observed by confocal optics or multi-photon excitation.

The detectability limits of a fluorophore were probed using simple sample geometry with TIRF measurements and very modest optics. Additionally, the excitation power was restricted to that achievable with simple laser diodes or LED's. This is similar to what is planned for our SPCE studies. Rhodamine 800 (Rh 800) was chosen as a test fluorophore because of its long absorption and emission wavelengths which extend beyond the hemoglobin absorption bands. Also, Rh 800 can be excited with inexpensive red laser diodes (commonly used for laser pointers).

As an excitation source we used a common laser pointer (633 nm, ~3 mW). Samples with different concentrations of Rh 800 in water, plasma and blood were placed in a demountable cuvette. The back plate of the cuvette has a thickness of 5 mm (all four sides polished), so excitation can enter from a side to form the angle grater than critical angle ($\alpha > \alpha c$) with the front surface. FIG. 8 shows the fluorescence intensity levels for various concentrations of Rh 800 in water, plasma and blood. Also shown are the number of observed molecules calculated from spot size and penetration depth. Concentration below 1 nM are readily observed in water (signal/background of 2). However, the concentrations for signal-to-background of 2 are near 5 nM and 30 nM in plasma and blood, respectively.

Calculated numbers of observed molecules are atop the vertical bars in FIG. 8. For water 18,000 Rh 800 molecules are easily detected. This number is significantly higher for plasma and blood because of significant background. But even for blood 210,000 molecules is reasonable number to be positioned on the surface of approximately 1 mm2. Since SPCE is more sensitive with less background, with the simple detection device, detection limits well below these values should be very achievable.

Figure 9:
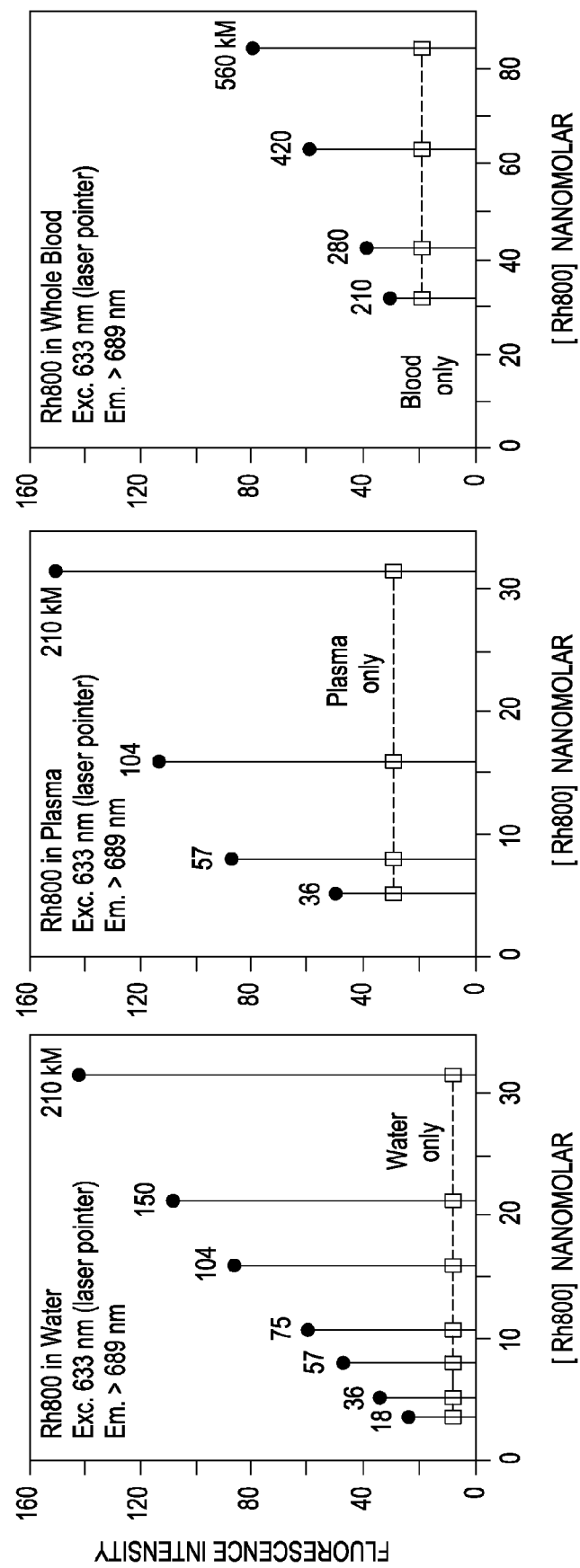
FIG. 9. Fluorescence signal from Rh800 in water, plasma, and whole blood with laser diode excitation at 633 nm.

FIG. 9 is the fluorescence signal from Rh800 in water, plasma, and whole blood with laser diode excitation at 633 nm. It is important to stress that presented measurements were done using clean quartz surface without any metal enhancement effect that would be available with SPCE. Fluorescent dye was in bulk solution, not bound to surface further reducing sensitivity relative to SPCE where the analyte is bound to the surface. With these factors in mind, the detection limits in FIG. 9 are probably much higher then that expected for dye deposited on surface within the enhancement layer as detected by SPCE.

A system with Cy3 and Cy5 labeled oligonucleotides was designed and tested by solution and TIRF fluorescence measurements. The effect of hybridization and FRET from Cy3 to Cy5 has been shown. By TIRF measurements with this system, an unlabeled oligo was detected ratiometrically in very sensitive fashion. In this ratiometric technique, the detected signal (ratio of intensities) depends only on the ratio and not number of sample molecules can be obtained. From data in the background and preliminary results sections SPCE will work for this system and do so with much more sensitivity.

Wavelength-resolved SPCE is a very sensitive and reliable technology for ratiometric sensing and detection of surface bound oligo-DNA strands in clean buffers and in a 'dirty matrix' such as reconstituted plasma and cell extracts (source of miRNA). About 100-fold and 10-fold improvements over solution and TIRF techniques, respectively, will be shown in terms of lower detectable concentrations. (See FIG. 1a)

Initially, the hybridization process was tested in SPCE configuration. The findings indicate that SPCE is a nearly perfect technology for this application. First, data using TIRF showed that surface confined technology is very well suited to this surface based assay. Second, earlier SPCE studies (8, 10) demonstrated that binding of a labeled oligo to an unlabeled complementary strand bound to surface can be conveniently detected by SPCE. Therefore, two color emissions can be separated and that the ratiometric assay made reliable. Reliability can be shown by accuracy and reproducibility in comparison with TIRF analyses. Sensitivity can be measured by the lowest concentration at which a signal/background ratio of 2 is determined.

Sensitivity and reliability. The assay and system should be useable any condition or format. This for example includes dissociation (i.e. replacement) of labeled complementary strand. This requires heating of the sample solution to stimulate and speed the exchange hybridization process. However, this also has a degradation effect on avidin binding and part of the surface immobilized oligos escapes from the surface. TIRF experiments indicated that in heating to ~52° C. and cooling down to room temperature 10%-15% of the oligo detached permanently presumably by irreversibly dissociating from the surface. This is quite expected for even high affinity binding. Such perturbation is completely unacceptable for a simple intensity assay. However, this is acceptable for the ratiometric assay. That is, dissociation of surface attached strand does lower the overall signal but does not change the ratio. This is an innovation particularly when coupled with the simple device shown in FIG. 1b.

FIG. 10. Configuration for measuring angular intensity distribution for SPCE emission. Left—schematic of the configuration. Two excitation modes (Kretschman and Reverse Kretschman) are shown in the figure. Right—photograph of the setup.

Specific experiments will test different assay formats in SPCE configuration. The experimental configuration for studying SPCE intensity distribution is shown in FIG. 10. This must be determined to position the detectors. The movable arm with mounted fiber allows measurements of angular intensity distribution with high precision. This custom built stage as shown in FIG. 10 has been used by the PI and colleagues for many years (4, 7, 8, 10). The specific tests or detection formats are:

1. As has been tested with TIRF with a Cy5 labeled 21-mer oligo and hybridized Cy3 labeled 15-mer (as shown in Table 1). The sensitivity and reproducibility of the SPCE detection will be measured and compare with results from TIRF performed as in the preliminary results section.
2. The Cy3 and Cy5 dyes will be switched between the anchored and freestrands. A 21-mer oligo labeled with 5'-Cy3 and 5'-bioteg will be used. This strand will be immobilized on the surface as before. In this way the green emission will be immobilized on the surface while the hybridized 15-mero will be labeled with 3'-Cy5. This configuration should give greater intensity from Cy5 when excited only with 532 nm laser diode. This is because each oligo hybridized to the surface will have the Cy3 in close proximity and residual energy transfer will significantly increase the fluorescence of barely excited Cy5. This is also innovative. (After our tests with TIRF in the preliminary results section, it was realized that this could be more effective combination.)
3. In fashion similar to microchip assays where the detected oligo is also labeled with either Cy3 or Cy5, the complementary oligo will be labeled with Cy3 and anchored to the surface. The Cy5 labeled sample strand will then be added in a small volume and heated to effect hybridization. This scenario avoids the use of a displaceable, labeled strand and will show further flexibility of the ratiometric detection. It may also allow a single gene chip to be used to analyze cDNA from two sources, each with a different label.
4. Evaluate the possibility of a "sandwich" type assay. In this format, one color labeled oligo will be immobilized on the surface. A second (non complementary) oligo labeled with another color dye will be free in solution (FIG. 10a). Both labeled oligos will have regions of complementary sequences to an unlabeled third oligo to be detected. When the third oligo is added to the solution it will hybridize with both oligos serving as a bridge type linker (FIG. 10b). This brings the nonanchored labeled strand within detection range of SPCE. The SPCE signal associated with green oligo upon addition of the unlabeled free oligo will increase as it is hybridized through the added oligo to the surface. Also in this configuration the reverse arrangement of dyes will be tested.

FIG. 11. Scheme for a DNA sandwich assay. The well-controlled tests performed in these preliminary measurements will show the sensitivity of the method and also very precisely measure angular distributions for two color SPCE.

Figures 12A, 12B:
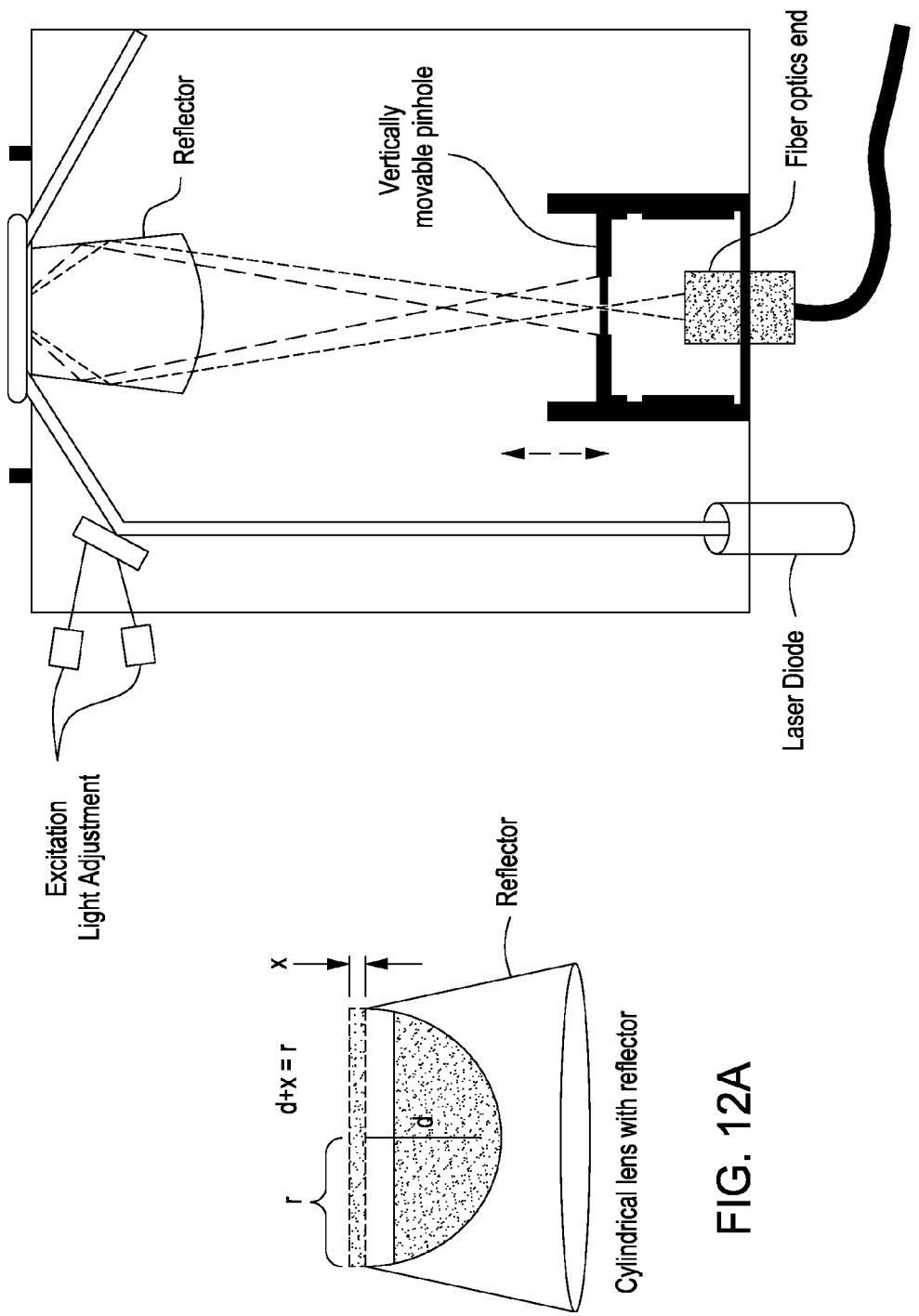
FIGS. 12A &12B shows a single pinhole detection device for SPCE.

A simple sensing device (FIG. 1(b)) was used with simple laser diode excitation (i.e. laser pointer) and photodiode detection. Having determined the exact angular distribution of SPCE for the emissions of Cy3 and Cy5 (and possibly other colors), the design of the prototype device can begin. A logical first step is to build a single pinhole device as shown in FIG. 12. This will allow the efficiency of the pinhole as a background suppressing element to be tested and optimized for hole size, thickness of material, etc. The reflector will focus the SPCE light emerging from the sample into a point. The position of the focus will directly depend on the angle under which the SPCE light is emerging from the sample. Moving the pinhole up and down it will select the red (Cy5) or green (Cy3) focus point. As in confocal microscopy, such a pinhole will dramatically reduce any ambient light emerging from the sample.

FIG. 12. Single pinhole detection device for SPCE. To produce the device shown in FIG. 12 the steps below will be performed. Design, produce, and test the coupling optics (half cylindrical lens from high refractive index glass integrated with the reflector. The design of the lens is also shown in FIG. 12. Coupling optics will be then integrated to the body of the device. For test studies in place of the inexpensive photodiode detector, fiber optics and no filter can be used as shown in FIG. 12. The end of fiber optics can be in the place of detector. The pinhole can be moved vertically as shown in FIG. 12. The fiber optics will deliver the signal into the fluormeter (single-photon counting system (PC1 from ISS) or alternatively to an Ocean Optics detector). As the pinhole moves the spectrum of transmitted light will be measured to evaluate how well the different colors can be separated. The observed spectrum will depend on the pinhole position. This will confirm the selective nature of the pinhole.

The SPCE detection device may be further optimized and refined in terms of overall size, adaptation to other optical systems, sample size, and limits of detection particularly in dirty matrices. Any application, such as immunological assays, which could benefit from the very low detection volume of SPCE will be used.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Gryczynski, I.; Malicka, J.; Gryczynski, Z.; Lakowicz, J. R., Surface plasmon-coupled emission: A new method for sensitive fluorescence detection. In Topics in fluorescence, Metal-Enhanced fluorescence, Lakowicz, J.; Geddes, C. D., Eds. Kluwer Academic/Plenum Publishers: 2005; Vol. 8, pp 381-403.
2. Gryczynski, Z.; Gryczynski, I.; Matveeva, E.; Malicka, J.; Nowaczyk, K.; Lakowicz, J. R., Surface-plasmon-coupled emission: new technology for studying molecular processes. Methods Cell Biol 2004, 75, 73-104.
3. Lakowicz, J. R., Radiative decay engineering 3. Surface plasmon-coupled directional emission. Anal Biochem 2004, 324, (2), 153-69.
4. Lakowicz, J. R.; Malicka, J.; Gryczynski, I.; Gryczynski, Z., Directional surface plasmon-coupled emission: A new method for high sensitivity detection. Biochem Biophys Res Commun 2003, 307, (3), 435-9.
5. Calander, N., Theory and simulation of surface plasmon-coupled directional emission from fluorophores at planar structures. Anal Chem 2004, 76, (8), 2168-73.
6. Neogi, A.; Morkoc, H.; Kuroda, T.; Tackeuchi, A., Coupling of spontaneous emission from GaN-AlN quantum dots into silver surface plasmons. Opt Lett 2005, 30, (1), 93-5.
7. Gryczynski, I.; Malicka, J.; Gryczynski, Z.; Lakowicz, J.; Malicka, I., Surface plasmon-coupled emission using gold film. J. Phys. Chem. B 2004, 108, 12568-12574.
8. Gryczynski, I.; Malicka, J.; Gryczynski, Z.; Lakowicz, J. R., Radiative decay engineering 4. Experimental studies of surface plasmon-coupled directional emission. Anal Biochem 2004, 324, (2), 170-82.
9. Malicka, J.; Gryczynski, I.; Fang, J.; Kusba, J.; Lakowicz, J. R., Increased resonance energy transfer between fluorophores bound to DNA in proximity to metallic silver particles. Anal Biochem2003, 315, (2), 160-9.
10. Malicka, J.; Gryczynski, I.; Gryczynski, Z.; Lakowicz, J. R., Use of surface plasmon-coupled emission to measure DNA hybridization. J Biomol Screen 2004, 9, (3), 208-15.
11. Borejdo, J.; Calander, N. G., Z.; Gryczynski, I., Fluorescence Correlation Spectroscopy in Surface Plasmon Coupled Emission Microscope. Optics Express 2006, 14, (17), 7878-7888.
12. Gryczynski, Z.; Borejdo, J.; Calander, N.; Matveeva, E. G.; Gryczynski, I., Minimization of detection volume by surface-plasmon-coupled emission. Anal Biochem 2006, 356, (1), 125-31.
13. Gryczynski, Z.; Gryczynski, I.; Lakowicz, J. R., Fluorescence-sensing methods. Methods Enzymol 2003, 360, 44-75.
14. Frey, B. L.; Jordan, C. E.; Kornguth, S.; Corn, R. M., Control of the specific adsorption of proteins onto gold surfaces with poly(1-ysine) monolayers. Anal. Chem. 1995, 67, 4452-4457.
15. Frutos, A. G.; Corn, R. M., SPR of ultrathin organic films. Anal. Chem. 1998, 449A-455A.
16. Jordan, C. E.; Frey, B. L.; Kornguth, S.; Corn, R. M., Characterization of Poly-L-lysine adsorption onto alkanethiol-modified gold surfaces with polarization-modulation fourier transform infrared spectroscopy and surface plasmon resonance measurements. Langmuir 1994, 10, 3642-3648.
17. Liedberg, B.; Lundstrom, I., Principles of biosensing with an extended coupling matrix and surface plasmon resonance. Sensors and Actuators B 1993, 11, 63-72.
18. Melendez, J.; Carr, R.; Bartholomew, D. U.; Kukanskis, K.; Elkind, J.; Yee, S.; Furlong, C.; Woodbury, r., A commercial solution for surface plasmon sensing. Sensors and Actuators B 1996, 35-36, 212-216.
19. Salamon, Z.; Macleod, H. A.; Tollin, G., Surface plasmon resonance spectroscopy as a tool for investigating the biochemical and biophysical properties of membrane protein systems. II: Applications to biological systems. Biochim Biophys Acta 1997, 1331, (2), 131-52.
20. Gryczynski, Z.; Matveeva, E.; Calander, N.; Zhang, J.; Lakowicz, J.; Gryczynski, I., Surface Plasmon Coupled Emission—Novel Technology for Studying Thin Layers of BioMolecular Assemblies. In Surface Plasmon Nanophotonics, Brongersma, M. L.; Kik, P. G., Eds. Springer: 2007; pp 247-265.
21. Barnes, W. L., Topical review: Fluorescence near interfaces: the role of photonic mode density. J. Modern Optics 1998, 454, (4), 661-699.
22. Lakowicz, J. R., Radiative decay engineering: biophysical and biomedical applications. Anal Biochem 2001, 298, (1), 1-24.
23. Lakowicz, J. R.; Shen, B.; Gryczynski, Z.; D'Auria, S.; Gryczynski, I., Intrinsic fluorescence from DNA can be enhanced by metallic particles. Biochem Biophys Res Commun 2001, 286, (5), 875-9.
24. Lakowicz, J. R.; Shen, Y.; D'Auria, S.; Malicka, J.; Fang, J.; Gryczynski, Z.; Gryczynski, I., Radiative decay engineering. 2. Effects of Silver Island films on fluorescence intensity, lifetimes, and resonance energy transfer. Anal Biochem 2002, 301, (2), 261-77.
25. Worthing, P. T.; Barnes, W. L., Spontaneous emission within metal-clad microcavities. J. Opt. A. Pure Appl. Opt. 1999, 1, 501-506.
26. Malicka, J.; Gryczynski, I.; Kusba, J.; Lakowicz, J. R., Effects of metallic silver island films on resonance energy transfer between N,N'-(dipropyl)-tetramethyl-indocarbocyanine (Cy3)- and N,N'-(dipropyl)-tetramethyl-indodicarbocyanine (Cy5)-labeled DNA. Biopolymers 2003, 70, (4), 595-603.
27. Borejdo, J.; Gryczynski, Z.; Calander, N.; Muthu, P.; Gryczynski, I., Application of surface plasmon coupled emission to study of muscle. Biophys J 2006, 91, (7), 2626-35.
28. Muthu, P.; Gryczynski, I.; Gryczynski, Z.; Talent, J.; Akopova, I.; Jain, K.; Borejdo, J., Decreasing photobleaching by silver island films: application to muscle. Anal Biochem 2007, 366, (2), 228-36.
29. miRBase::Sequences. http://microrna.sanger.ac.uk/cgi-bin/sequences/browse.pl (Jul. 31, 2007),
30. Gryczynski, I.; Gryczynski, Z.; Lakowicz, J. R., Two-photon excitation by the evanescent wave from total internal reflection. Anal Biochem 1997, 247, (1), 69-76.
31. Lakowicz, J. R.; Gryczynski, Z.; Gryczynski, I., On the possibility of evanescent wave excitation distal from a solid-liquid interface using light quenching. Photochem Photobiol 1996, 64, (4), 636-41.
32. Matveeva, E.; Gryczynski, Z.; Malicka, J.; Gryczynski, I.; Lakowicz, J. R., Metal-enhanced fluorescence immunoassays using total internal reflection and silver island-coated surfaces. Anal Biochem 2004, 334, (2), 303-11.
33. Enderlein, J.; Robbinson, D. L.; Ambrose, W. P.; Keller, R. A., Molecular shot noice, burst size distribution, and single-molecule detection in fluid flow. Effect of multiple occupancy. J. Phys. Chem. A 1998, 102, 6089.
34. Erdman, R.; Enderlein, J.; Siedel, C., Single molecule detection and ultrasensitive analysis in the life science. Cytometry 1999, 36, (3), 161-164.

What is claimed is:

1. A method for ratiometric surface plasmon coupled emission detection comprising:
   disposing a target on the metal layer of a surface plasmon resonance detection system;
   coupling at least a first analyte to a first fluorescent dye and at least a second analyte to a second fluorescent dye;
   contacting the first and second analytes to the target on the surface plasmon resonance detection system; and
   measuring the intensity of a first and a second surface plasmon resonance enhanced fluorescence emission ring, wherein the first and second rings, respectively, quantitatively represents the amount of first and second analyte within 50 nanometers of the metal surface.

2. The method of claim 1, wherein the at least first and second fluorescent dyes are selected from 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone and Yellow fluorescent protein.

3. The method of claim 1, wherein the first and second analytes are selected from nucleic acids, polynucleotides, amino acids, peptides, polypeptides, lipids, carbohydrates, vitamins, minerals, cells and tissues and combinations thereof.

4. The method of claim 1, wherein the surface plasmon resonance detection system comprises a Reverse Kretschmann configuration.

5. The method of claim 1, wherein the surface plasmon resonance detection system comprises a Kretschmann configuration.

6. The method of claim 1, wherein the surface plasmon resonance detection system comprises one or more light sources that do not interfere with the emission spectra of the first and second dyes.

7. The method of claim 1, wherein the surface plasmon enhanced molecules further comprise chemiluminescent emissions, bioluminescent emissions, electrochemiluminescent emissions, fluorescent resonance emissions and combinations thereof.

8. The method of claim 1, wherein the target is within a cell.

9. A method for ratiometric surface plasmon coupled emission detection comprising:
   disposing a target on the metal layer of a surface plasmon resonance detection system, the surface plasmon resonance detection system comprising:
   a light translucent material;
   a metal layer disposed on the light translucent material, wherein the thickness of the metal layer is 50 nM or less;

a glass prism disposed on the light translucent material opposite the metal layer;

a light source capable of exciting two or more surface plasmon enhanced molecules, the excitation source positioned to strike the light translucent material at a first angle; and a light detector that detects emitted light generated by the two or more surface plasmon enhanced molecules at a first and a second angle;

coupling two or more target specific fluorophores for detection of two or more specific targets in a sample;

contacting the two or more target specific fluorophores to the targets in the sample, wherein the sample is on the metal layer; and measuring the intensity of a first and a second surface plasmon resonance p-polarized enhanced fluorescence emission ring for each of the two or more fluorophores, wherein each of the two or more fluorophores generates a separate fluorescence emission ring that quantitatively represents the amount of binding to the two or more targets within 50 nanometers of the metal layer.

10. The method of claim 9, wherein the at least two or more fluorescent dyes are selected from 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9,10-bis(phenylethynyl)anthracene; 2-Chloro-9,10-bis(phenylethynyl) anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone and Yellow fluorescent protein.

11. The method of claim 9, wherein the two or more analytes are selected from nucleic acids, polynucleotides, amino acids, peptides, polypeptides, lipids, carbohydrates, vitamins, minerals, cells and tissues and combinations thereof.

12. The method of claim 9, wherein the surface plasmon resonance detection system comprises a Reverse Kretschmann configuration.

13. The method of claim 9, wherein the surface plasmon resonance detection system comprises a Kretschmann configuration.

14. The method of claim 9, wherein the surface plasmon resonance detection system comprises one or more light sources that do not interfere with the emission spectra of the first and second dyes.

15. The method of claim 9, wherein the surface plasmon enhanced molecules comprise fluorescent dyes, chemiluminescent emissions, bioluminescent emissions, electrochemiluminescent emissions, fluorescent resonance emissions and combinations thereof.

16. The method of claim 9, wherein the light source is selected from filtered white light sources, ultraviolet lamps, lasers (gas or semiconductor) and light emitting diode(s) (LEDs).

17. The method of claim 9, wherein the target is within a cell.

* * * * *